United States Patent
Ji et al.

(10) Patent No.: US 11,091,509 B2
(45) Date of Patent: Aug. 17, 2021

(54) HPPK INHIBITORS USEFUL AS ANTIBACTERIAL AGENTS

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Xinhua Ji, Frederick, MD (US); Genbin Shi, Frederick, MD (US); Gary X. Shaw, North Potomac, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 15 days.

(21) Appl. No.: 16/340,493

(22) PCT Filed: Oct. 11, 2017

(86) PCT No.: PCT/US2017/056124
§ 371 (c)(1),
(2) Date: Apr. 9, 2019

(87) PCT Pub. No.: WO2018/071531
PCT Pub. Date: Apr. 19, 2018

(65) Prior Publication Data
US 2019/0241605 A1 Aug. 8, 2019

Related U.S. Application Data

(60) Provisional application No. 62/406,610, filed on Oct. 11, 2016.

(51) Int. Cl.
| | | |
|---|---|---|
| C07H 19/167 | (2006.01) | |
| C07H 19/16 | (2006.01) | |
| C07D 475/04 | (2006.01) | |
| A61P 31/04 | (2006.01) | |

(52) U.S. Cl.
CPC ............ *C07H 19/167* (2013.01); *A61P 31/04* (2018.01); *C07D 475/04* (2013.01); *C07H 19/16* (2013.01)

(58) Field of Classification Search
None
See application file for complete search history.

(56) References Cited

U.S. PATENT DOCUMENTS

| 4,036,961 A | 7/1977 | Stuart | |
| 9,029,344 B2 * | 5/2015 | Shi | C07D 475/04 514/46 |
| 2015/0218167 A1 | 8/2015 | Shi et al. | |

FOREIGN PATENT DOCUMENTS

| EP | 0884317 B1 | 5/2005 | |
| FR | 2215964 | 8/1974 | |
| JP | 06056669 | 1/1994 | |
| WO | 2011159471 A2 | 12/2011 | |
| WO | WO-2011159471 A2 * | 12/2011 | ............. G16B 15/00 |

OTHER PUBLICATIONS

Al-Hassan, S. et al. "Specific Inhibitors in Vitamin Biosynthesis. Part 7. Syntheses of Blocked 7,8-Dihydropteridines via a-Amino Ketones", Journal of the Chemical Society, Perkin Transactions 1, Jan. 1, 1985, pp. 1645-1659.
Blaszczyk, J. et al. "Catalytic Center Assembly of HPPK as Revealed by the Crystal Structure of a Ternary Complex at 1.25 Å Resolution" Structure, vol. 8, Oct. 2000, pp. 1049-1058.
Blaszczyk, J. et al. "Reaction Trajectory of Pyrophosphoryl Transfer Catalyzed by 6-Hydroxymethyl-7,8-Dihydropterin Pyrophosphokinase" Structure, vol. 12, 2004, pp. 467-475.
Brown, R. et al. "Synthesis and Reactions of 7,8-Diydro-8-methylpterin and 9-Methyl-guanine 7-Oxide", Journal of the Chemcial Society, Perkin Transactions 1, No. 9, Jan. 1, 1977, pp. 1003-1009.
Hennig, M. et al. "The Structure and Function of the 6-Hydroxymethyl-7,8-dihydropterin Pyrophosphokinase From Haemophilus Influenzae" Journal of Molecular Biology, 1999, 287, pp. 211-219.
International Search Report dated Feb. 17, 2012; International Application No. PCT/US2011/038744; International Filing Date: Jun. 1, 2011 (6 Pages).
International Search Report dated Nov. 28, 2017; International Application No. PCT/US2017/056124; International Filing Date Oct. 11, 2017 (5 pages).
Mengel, R., et al., "Pteridine, LXVI: Synthese und Eigenschaften von Dihydro- und Tetrahydro- Derivaten der Pterin-6,7-dicarbonsaure*)", with English Abstract, Chemische Bericht, vol. 111, No. 12, Dec. 1, 1978, pp. 3790-3805.

(Continued)

*Primary Examiner* — Traviss C McIntosh, III
(74) *Attorney, Agent, or Firm* — Cantor Colburn LLP

(57) ABSTRACT

The disclosure provides linked purine pterin compounds of Formula I that are novel inhibitors of HPPK, a kinase responsible for an essential step in the biosynthesis of folic acid. (Formula I) The variables, e.g., A1-A3, R1-R4, B1-B2, and L1 are defined in the disclosure. These linked purine pterin inhibitors bind to HPPK with high affinity and specificity. Pharmaceutical compositions containing the HPPK inhibitors and methods of treating a bacterial infection in a patient with one or more of the HPPK inhibitors of the disclosure are also provided.

(I)

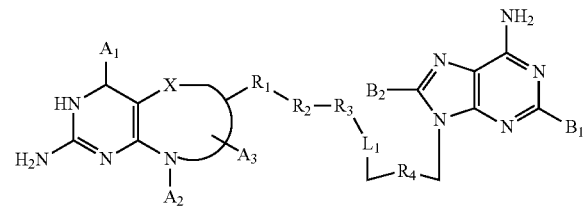

19 Claims, 2 Drawing Sheets

(56) References Cited

OTHER PUBLICATIONS

Shi, G. et al. "Bisubstrate Analogue Inhibitors of 6-Hydroxymethyl-7,8-dihydropterin Pyrophosphokinases: Synthesis and Biochemical and Crystallographic Studies" Journal of Medical Chemistry, vol. 44, 2000, pp. 1364-1371.

Shi, G. et al. "New Ways to Derivatize at Position 6 of 7,7-dimethyl-7,8-dihydropterin" Tetrahedron Letters, 52, 2011, pp. 6174-6176.

Wang, Y. et al. "A Point Mutation Converts Dihydroneopterin Aldolase to a Cofactor-Independent Oxygenases", Journal of the American Chemical Society, vol. 128, No. 40, Oct. 1, 2006, pp. 13216-13223.

Wood, H. "Specific Inhibition of Dihydrofolate Biosynthesis—A New Approach to Chemotherapy" Chemistry and Biology of Pteridines, 1975, pp. 27-49.

Written Opinion dated Feb. 17, 2012; International Application No. PCT/US2011/038744, International Filing Date: Jun. 1, 2011 (6 Pages).

Written Opinion dated Nov. 28, 2017; International Application No. PCT/US2017/056124; International Filing Date Oct. 11, 2017 (7 pages).

\* cited by examiner

HPPK INHIBITORS USEFUL AS ANTIBACTERIAL AGENTS

CROSS-REFERENCE TO RELATED APPLICATIONS

This application is a National Stage application of PCT/US2017/056124, filed Oct. 11, 2017, which claims the benefit of U.S. Provisional Application No. 62/406,610, filed Oct. 11, 2016, both of which are incorporated herein in their entireties by reference.

STATEMENT OF GOVERNMENT SUPPORT

This invention was made with government support under project number ZIA BC 010326 by the National Institutes of Health. The government has certain rights in the invention.

FIELD OF THE DISCLOSURE

The disclosure provides linked purine pterin compounds that are novel HPPK inhibitors. These linked purine pterin inhibitors bind to HPPK with high affinity and specificity. Pharmaceutical compositions containing HPPK inhibitors and methods of treating a bacterial infection in a patient with one or more of the HPPK inhibitors of the disclosure are also provided.

BACKGROUND

Folate cofactors are essential for life. Mammals derive folates from their diet, whereas most microorganisms must synthesize folates de novo. Therefore, the microbial folate pathway is an ideal target for developing anti-bacterial agents. For example, inhibitors of two enzymes in the pathway, dihydropteroate synthase and dihydrofolate reductase, are currently used as antibiotics. 6-Hydroxymethyl-7,8-dihydropterin pyrophosphokinase (E.C. 2.7.6.3, HPPK), a kinase responsible for an essential step in the biosynthesis of folic acid, catalyzes the transfer of pyrophosphate from ATP to 6-hydroxymethyl-7,8-dihydropterin (HP) to form the diphosphate, HPPP. (FIG. 1A)

To facilitate the phosphoryl transfer reaction shown in FIG. 1A, six amino acid side chains interact with the phosphate groups of ATP (FIG. 1B) in addition to $Mg^{2+}$-ion-mediated protein-phosphate interactions. Bisubstrate analog inhibitors that feature linked purine and pterin moieties were previously identified. A diagram showing the interaction of —S-[1-(2-{[(2-amino-7,7-dimethyl-4-oxo-3,4,7,8-tetrahydropteridin-6-yl)carbonyl]amino}ethyl)piperidin-4-yl]-5'-thioadenosine, a previously identified HPPK inhibitor shown in FIG. 1C. A diagram showing the interactions of 2-amino-7,7-dimethyl-4-oxo-3,4,7,8-tetrahydropteridine-6-carboxylic acid (2-{2-[5-(6-amino-purin-9-yl)-3,4-dihydroxy-tetrahydro-furan-2-ylmethanesulfonyl]-ethylcarbamoyl}-ethyl)-amide with HPPK is provided in FIG. 1D. Even though the linkers of the compounds shown in FIG. 1D do not interact with the protein their affinities to the enzyme are comparable with ATP. Any further improvement in linkage-protein interactions will enhance the potency of the inhibitors well above that of the substrate and cofactor of HPPK.

Due to in-depth structural and mechanistic studies of HPPK, this enzyme is well understood and therefore a good target for novel anti-bacterial compounds. [0003] HPPK inhibitors have been reported, but none have yet entered clinical use. Thus, there remains a need for novel and useful HPPK inhibitor anti-bacterial compounds. Using structure-based approach, we have developed transition state analog HPPK inhibitors with significantly improved potency. The present disclosure fulfills the need for improved HPPK inhibitors and provides further advantages, which are set forth below.

SUMMARY

The disclosure provides a compound of Formula I

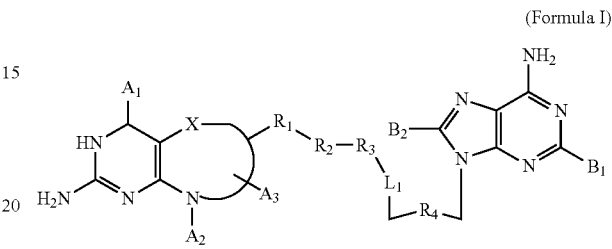

(Formula I)

and the pharmaceutically acceptable salts thereof are provided herein. Within Formula I, the variables, e.g. X, $A_1$, $A_2$, $A_3$, $R_1$, $R_2$, $R_3$, $R_4$, $L_1$, $B_1$, and $B_2$, carry the following definitions.

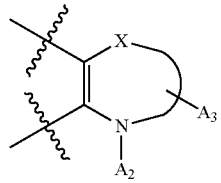

is a 5 or 6-membered heterocyclic ring.

X is nitrogen, —N($A_5$)—, —C($A_6$)—, or —C($A_6A_7$)—.
$A_1$ is hydrogen, oxo, amino, or amino$C_1$-$C_2$alkyl.
$A_2$ is absent, hydrogen, or $C_1$-$C_2$alkyl.
$A_3$ is absent, or one or two substituents independently chosen from hydrogen, halogen, $C_1$-$C_2$alkyl, and $C_1$-$C_2$alkoxy.
$A_5$ is hydrogen or $C_1$-$C_4$alkyl.
$A_6$ and $A_7$ are independently hydrogen, $C_1$-$C_4$alkyl, or $C_1$-$C_4$alkoxy.
$R_1$ is $C_1$-$C_4$alkylene optionally substituted with hydroxyl, halogen, $C_1$-$C_2$alkyl, or oxo.
$R_2$ is chosen from —NH—, —NHC(=O)—, —SH—, —S(=O)—, —S(=O)$_2$—, —P(=O)—, and —P(=O)$_2$—.
$R_3$ is —N($R_5$)—, —($C_1$-$C_4$alkyl)N($R_5$)— or —($C_1$-$C_4$alkyl)C(O)N$R_5$)—, where $R_5$ is alkyl substituted with —P(O)(OH)$_2$, —OP(O)(OH)$_2$, or COOH;
$R_3$ is a 5- or 6-membered heterocycloalkyl containing 1 or 2 heteroatoms independently chosen from N, O, and S, which 5- or 6-membered heterocycloalkyl is unsubstituted or substituted with 1 or more substituents independently chosen from hydroxyl, halogen, amino, —COOH, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy; or $R_3$ is —($C_1$-$C_4$alkyl)heterocycloalkyl; which heterocycloalkyl is a 5- or 6-membered heterocycloalkyl containing 1 or 2 heteroatoms independently chosen from N, O, and S, and is substituted with at least one —($C_0$-$C_4$alkyl)P(O)(OH)$_2$, —($C_0$-$C_4$alkyl)OP(O)(OH)$_2$, or —($C_0$-$C_4$alkyl)COOH, or —($C_0$-$C_4$alkyl)C(=O)O($C_1$-$C_4$alkyl), and optionally substituted with 1 or more substituents independently chosen from hydroxyl, halogen, amino, —COOH, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

$L_1$ is an alkylene linker having from 1 to 4 containing 1 group selected from —O—, —NH—, —S—, —S(=O)—, —S(=O)$_2$—, —S(=O)$_2$NH—, —C(=O)NH—, —P(=O)—, and —P(=O)$_2$—; and optionally containing 1 to 2 carbon-carbon double bonds, wherein $L_1$ is unsubstituted or substituted with 1 or more substituents independently chosen from hydroxyl, halogen, amino, $C_1$-$C_4$alkyl, $C_1$-$C_4$alkoxy, $C_1$-$C_2$haloalkyl, and $C_1$-$C_2$haloalkoxy.

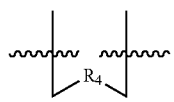

is a 5- or 6-membered monosaccharide ring.

$B_1$ and $B_2$ are independently chosen from hydrogen, halogen, hydroxyl, amino, $C_1$-$C_2$alkyl, $C_1$-$C_2$alkoxy, mono- or di-$C_1$-$C_2$alkylamino, amino$C_1$-$C_2$alkyl, $C_1$-$C_2$haloalkyl, and $C_1$-$C_2$haloalkoxy.

Pharmaceutical compositions comprising a compound or salt of Formula I together with a pharmaceutically acceptable carrier are further provided herein.

A method of treating a condition responsive to HPPK modulation, comprising providing a therapeutically effective amount of compound of Formula I or any of the embodiments of this disclosure to a patient having a condition response to HPPK modulation is also provided herein. Conditions responsive to HPPK modulation include bacterial infections.

BRIEF DESCRIPTION OF THE DRAWINGS

FIG. 1A. The pyrophosphoryl transfer catalyzed by HPPK and chemical structures of the substrate and product of the reaction.

FIG. 1B. Interactions between HPPK and ATP in the active site of the catalytic assembly.

FIG. 1C. Chemical structure of an early bisubstrate analogue inhibitor and its interaction with ATP-binding side chains of HPPK.

FIG. 1D. Chemical structure of another early bisubstrate analogue inhibitor and its interaction with ATP-binding side chains of HPPK.

FIG. 2A. Chemical structure of Compound 114 and its interaction with ATP-binding side chains as observed in the HPPK:compound 114 structure.

FIG. 2B. Chemical structure of Compound 118 and its interaction with ATP-binding side chains as observed in the HPPK:compound 118 structure. Residues without dashed lines to the inhibitors do not interact with the inhibitors.

DETAILED DISCLOSURE

Terminology

Figure 1A:
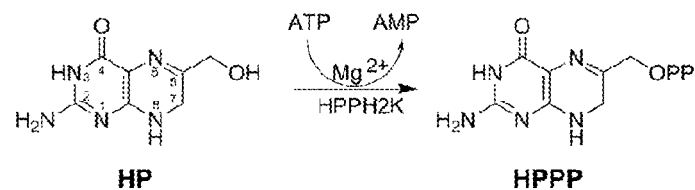
FIGS. 1A-D show the HPPK-catalyzed reaction and bisubstrate analogue inhibitors of the enzyme.

Presently disclosed compounds are described using standard nomenclature. Unless defined otherwise, all technical and scientific terms used herein have the same meaning as is commonly understood by one of skill in the art to which this disclosure belongs. Unless clearly contraindicated by the context each compound name includes the free acid or free base form of the compound as all pharmaceutically acceptable salts of the compound.

The phrase "compounds of Formula I" encompasses all compounds that satisfy Formula I, including any enantiomers, racemates and stereoisomers, as well as all pharmaceutically acceptable salts of such compounds and also includes all subgeneric groups of Formula I, unless clearly contraindicated by the context in which this phrase is used.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate and does not pose a limitation on the scope of the disclosure unless otherwise claimed. No language in the specification should be construed as indicating any non-claimed element as essential to the practice as used herein. Unless defined otherwise, technical and scientific terms used herein have the same meaning as is commonly understood by one of skill in the art to which this disclosure belongs.

An "active agent" means a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

A dash ("-") that is not between two letters or symbols is used to indicate a point of attachment for a substituent. For example, —(C=O)NH$_2$ is attached through carbon of the keto (C=O) group.

A bond represented by a combination of a solid and dashed line, i.e., =====, may be either a single or double bond.

"Alkyl" is a branched or straight chain saturated aliphatic hydrocarbon group, having the specified number of carbon atoms, generally from 1 to about 12 carbon atoms. The term $C_1$-$C_6$alkyl indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_5$alkyl, $C_1$-$C_4$alkyl, and $C_1$-$C_2$alkyl. When $C_0$-$C_n$ alkyl is used herein in conjunction with another group, for example, "Alkylene" is a saturated organic radical of the formula —(CH$_2$)$_n$— where n is the number of CH$_2$ groups in the alkylene radical. Alkylene radicals having from 1 to 6 carbons or from 1 to 4 carbons are usually preferred. Likewise "heteroalkylene" is a saturated organic radical of the formula —(CH$_2$)$_n$— where n is the number of CH$_2$ groups in the chain and the alkylene chain is interrupted at one or more points, usually one point, with a covalently bound heteroatom selected from nitrogen, oxygen, sulfur, and phosphorous.

"Alkoxy" is an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Haloalkyl" is both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined herein attached through an oxygen bridge (oxygen of an alcohol radical).

"Halo" or "halogen" is any of fluoro, chloro, bromo, and iodo.

"Heterocycloalkyl" is a saturated monocyclic group having the indicated number of ring atoms and containing from 1 to about 3 heteroatoms chosen from N, O, and S, with remaining ring atoms being carbon, or a saturated bicyclic ring system having at least one N, O, or S ring atom with the remaining atoms being carbon. Monocyclic heterocycloalkyl groups usually have from 4 to about 8 ring atoms. In some embodiments monocyclic heterocycloalkyl groups have from 5 to 7 ring atoms. Heterocycloalkyl groups include piperazine, piperidine, morpholine, thiomorpholine, tetrahydropyran, pyrrolidine, imidazolidine, and tetrahydrofuran.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

A "monosaccharide" is any of several carbohydrates, such as tetroses, pentoses, and hexoses, which cannot be broken down to simpler sugars by hydrolysis. When a monosaccharide is recited as a component of Formula I a divalent radical of a monosaccharide is intended. Such a monosaccharide is covalently bound through the oxygen atoms of two of its hydroxyl groups to the purine nitrogen and $L_1$.

The term "substituted" means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified, substituents are named into the core structure. For example, it is to be understood that when aminoalkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g., coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like.

The term "carrier" applied to pharmaceutical compositions of the disclosure refers to a diluent, excipient, or vehicle with which an active compound is provided. An excipient is an inactive ingredient useful in preparing a pharmaceutical composition that is generally safe, non-toxic, and neither biologically nor otherwise undesirable, and includes an excipient that is acceptable for veterinary use as well as human pharmaceutical use.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment" as used herein includes providing a compound of Formula I, either as the only active agent or together with at least one additional active agent sufficient to: (a) inhibiting the disease, i.e., arresting its development; and (b) relieving the disease, i.e., causing regression of the disease. Bacterial infections, such as bacterial infections and fungal infections, are included in the diseases treated with a compound of Formula I. "Treating" and "treatment" also means providing a therapeutically effective amount of a compound of Formula I, as the only active agent or together with at least one additional active agent to a patient having a bacterial infection.

A "therapeutically effective amount" of a compound of Formula I or composition of this disclosure means an amount effective, when administered to a patient, to provide a therapeutic benefit such as an amelioration of symptoms, e.g., an amount effective to decrease the symptoms of a bacterial infection. For example a patient having a bacterial infection may present elevated levels of certain liver enzymes or an elevated white blood cell count. A therapeutically effect amount is thus an amount sufficient to provide a significant reduction in elevated liver enzyme levels or white blood cell count, or an amount sufficient to provide a return of the liver enzyme levels or white blood cell count to the normal range. A therapeutically effective amount is also an amount sufficient to prevent a significant increase or significantly reduce the detectable level of bacterial particles or anti-bacterial antibodies in the patient's blood, serum, or tissues.

A "significant reduction" in the detectable level of bacterial particles or anti-bacterial antibodies is any detectable reduction that is statistically significant in a standard parametric test of statistical significance such as Student's T-test, where $p<0.05$.

Chemical Description

Formula I includes all subformula thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present disclosure. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent or chromatography, using, for example, a chiral high pressure liquid chromatography (HPLC) column.

Where a compound exists in various tautomeric forms, the disclosure is not limited to any one of the specific tautomers, but rather includes all tautomeric forms.

The present disclosure is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g., X, $A_1$, $A_2$, $A_3$, $R_1$, $R_2$, $R_3$, $R_4$, $L_1$, $B_1$, and $B_2$. Unless otherwise specified, each variable within such a formula is defined independently of other variables. Thus, if a group is said to be substituted, e.g., with 0-2 R*, then the group may be substituted with up to two R* groups and R* at each occurrence is selected independently from the definition of R*. Also, combinations of substituents and/or variables are permissible only if such combinations result in stable compounds.

In addition to compounds of Formula I as described above, the disclosure also includes compounds of Formula I in which one or more of the following conditions is met for the variables in Formula I. Embodiments of this disclosure include any combination of conditions listed below, so long as a stable compound results.

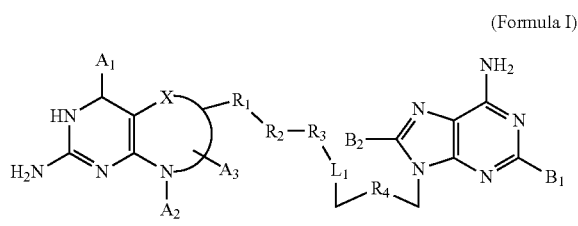

(Formula I)

Compounds having any combination of the variable definitions set forth below that result in a stable compound are included in the disclosure.

When the group

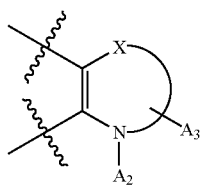

is a 6-membered ring, $R_1$ is preferably attached at the 6-position, that is at the atom adjacent to X, for example the moiety

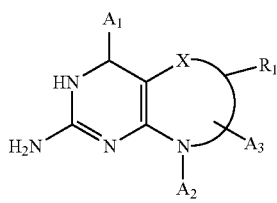

can be a group such as

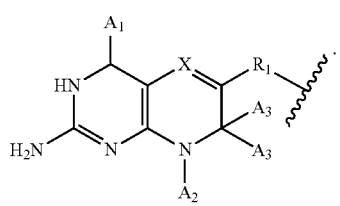

When the group

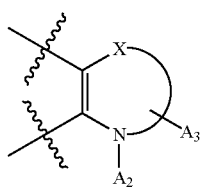

is a 5-membered ring, $R_1$ is preferably attached at the 5-position, that is at X, for example the moiety

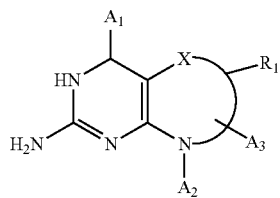

can be a group such as

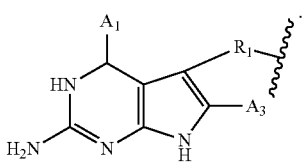

The disclosure also includes compounds of Formula II-Formula XI.

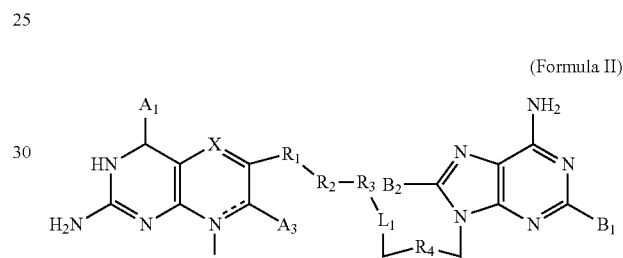

(Formula II)

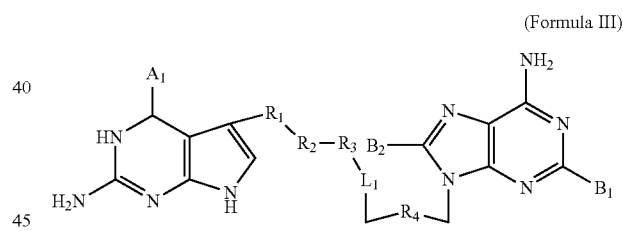

(Formula III)

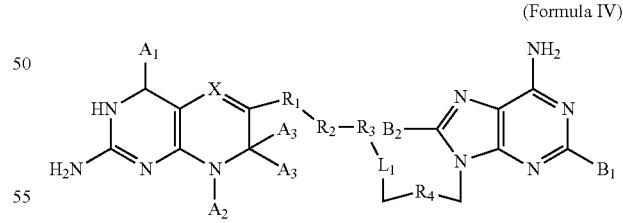

(Formula IV)

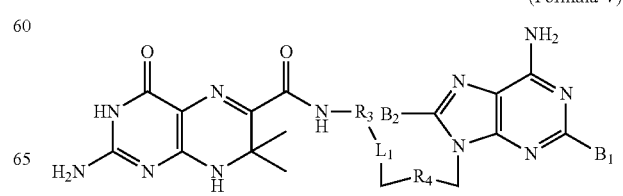

(Formula V)

-continued

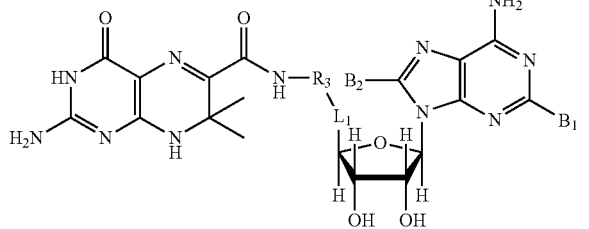
(Formula VI)

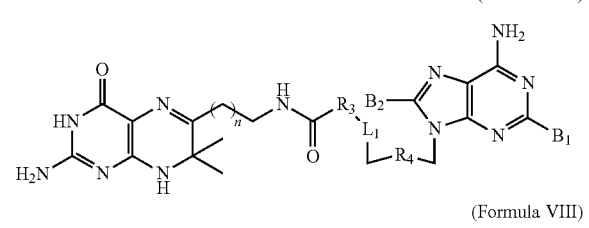
(Formula VII)

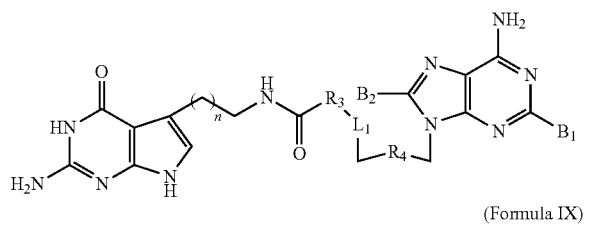
(Formula VIII)

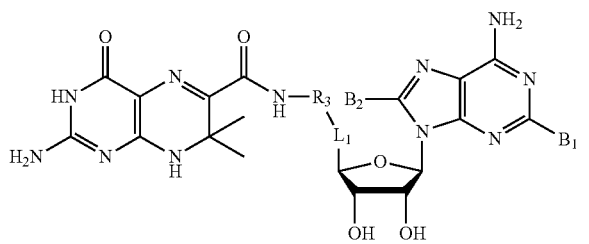
(Formula IX)

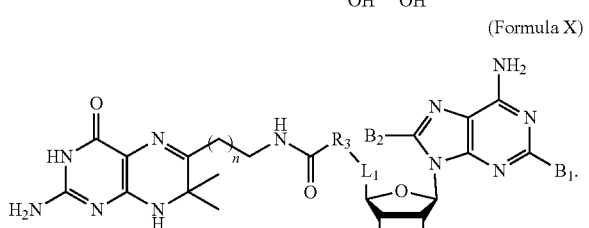
(Formula X)

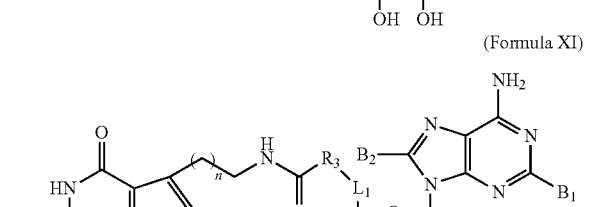
(Formula XI)

In Formula II, $A_2$ can be absent or hydrogen; $A_3$ can be one or two substituents independently chosen from hydrogen and $C_1$-$C_2$; and X can be N or —C($A_6$)—.

In Formula III, $A_3$ can be one or two substituents independently chosen from hydrogen and $C_1$-$C_2$ alkyl.

In Formula IV, $A_3$ can each independently be hydrogen, halogen, methyl, or methoxy. Optionally $A_2$ is hydrogen.

In Formula VII, n can be 0, 1, 2, or 3, or n can be 1 or 2.

In Formula VIII n can be 0, 1, 2, or 3, or n can be 1 or 2.

In any of Formula I to XI, $B_1$ and $B_2$ can both be hydrogen.

In any of Formula I to XI,

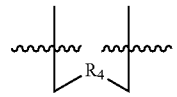

is a 5-membered monosaccharide ring. In certain embodiments the monosaccharide is substituted with a $C_1$-$C_6$alkyl or —C(O)$C_1$-$C_6$alkyl group. For example

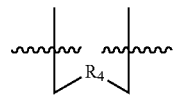

can be

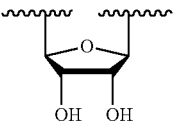

The Variable $R_3$

The disclosure includes compounds and salts of any of the above Formulas in which $R_3$ carries any of the following definitions:

(a) $R_3$ is a 5- or 6-membered heterocycloalkyl containing 1 or 2 heteroatoms independently chosen from N, O, and S, which — or 6-membered heterocycloalkyl is unsubstituted or substituted with 1 or more substituents independently chosen from hydroxyl, halogen, amino, —COOH, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

(b) $R_3$ is piperazine, piperidine, morpholine, thiomorpholine, tetrahydropyran, pyrrolidine, imidazolidine, or tetrahydrofuran, each of which is unsubstituted or substituted with 1 or more substituents independently chosen from hydroxyl, halogen, amino, —COOH, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

(c) $R_3$ is piperazine or piperidine group which is unsubstituted or substituted with 1 or more substituents independently chosen from hydroxyl, halogen, amino, —COOH, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

(d) $R_3$ is piperidine or piperazine, which $R_3$ is unsubstituted or substituted with one —COOH group.

(e) $R_3$ is —N($R_5$)—, —$C_1$-$C_4$alkylN($R_5$)—, or —$C_1$-$C_4$alkylC(O)N($R_5$)—, where $R_5$ is $C_1$-$C_4$alkyl substituted with —P(O)(OH)$_2$, —OP(O)(OH)$_2$, or COOH.

(f) $R_3$ is —N($R_5$)—, —$C_1$-$C_4$alkylN($R_5$)—, or —$C_1$-$C_4$alkylC(O)N($R_5$)—, where $R_5$ is $C_1$-$C_4$alkyl substituted with —P(O)(OH)$_2$, —OP(O)(OH)$_2$, or COOH.

(g) $R_3$ is —CH$_2$CH$_2$C(O)N(CH$_2$P(O)(OH)$_2$)—, —CH$_2$C(O)N(CH$_2$P(O)(OH)$_2$)—, —CH$_2$CH$_2$N(CH$_2$P(O)(OH)$_2$)—, or —N(CH$_2$P(O)(OH)$_2$)—.

(h) $R_3$ is —($C_1$-$C_4$alkyl)heterocycloalkyl in which the heterocycloalkyl is a 5- or 6-membered heterocycloalkyl containing 1 or 2 heteroatoms independently chosen from N, O, and S, and is substituted with at least one —(C$_0$-C$_4$alkyl)P(O)(OH)$_2$, —(C$_0$-C$_4$alkyl)OP(O)(OH)$_2$, —(C$_0$-C$_4$alkyl)COOH, or —(C$_0$-C$_4$alkyl)C(=O)O(C$_1$-C$_4$alkyl), and optionally substituted with 1 or more substituents independently chosen from hydroxyl, halogen, amino, —COOH, C$_1$-C$_4$alkyl, C$_1$-C$_4$alkoxy, mono- and di-C$_1$-C$_4$alkylamino, C$_1$-C$_2$haloalkyl, and C$_1$-C$_2$haloalkoxy.

R$_3$ is —(C$_1$-C$_4$alkyl)piperidine or —(C$_1$-C$_4$alkyl)piperazine, each of which piperidine or piperazine is unsubstituted or substituted with 1 or 2 —COOH groups.

The Variable L$_1$

The disclosure includes compounds and salts of any of the above Formulas in which L$_1$ carries any of the following definitions:

(a) L$_1$ is an alkylene linker having 2 to 4 carbon atom and containing one S atom, which S atom is optionally substituted with one or two oxo groups.

(b) L$_1$ is chosen from

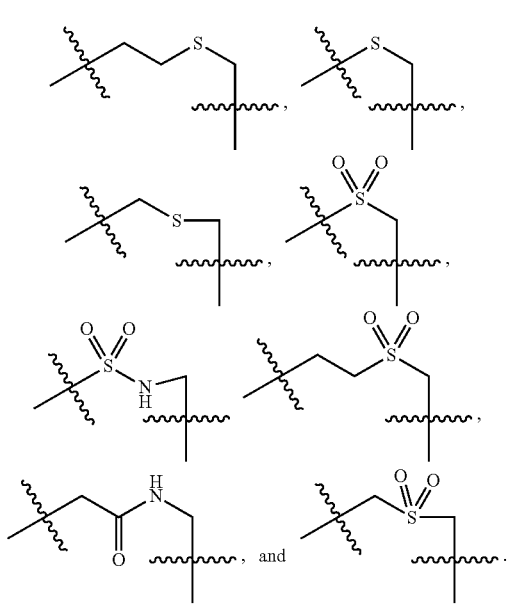

(c) L$_1$ is chosen from

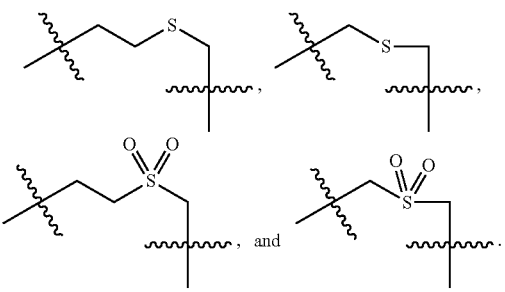

(d) L$_1$ is chosen from

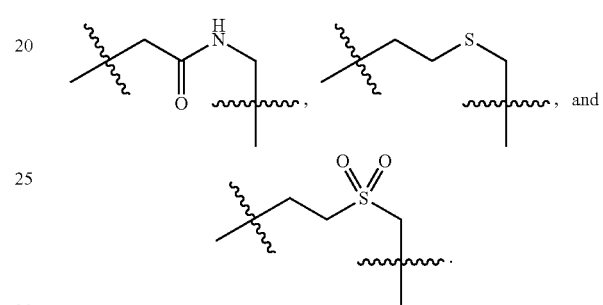

(e) L$_1$ is a linker chosen from

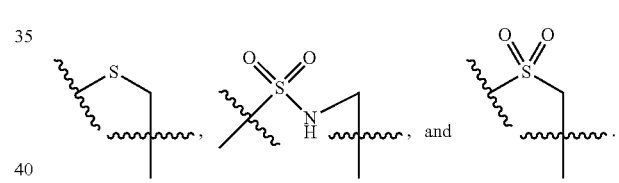

This disclosure includes the following compounds and their pharmaceutically acceptable salts:

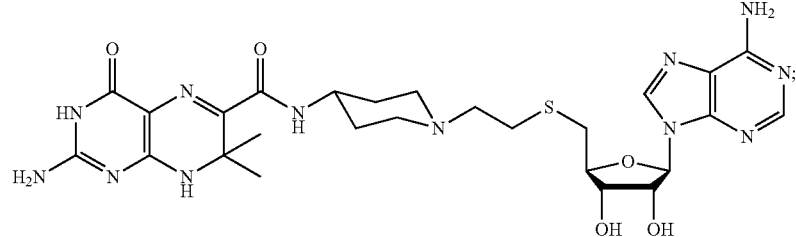

(101)

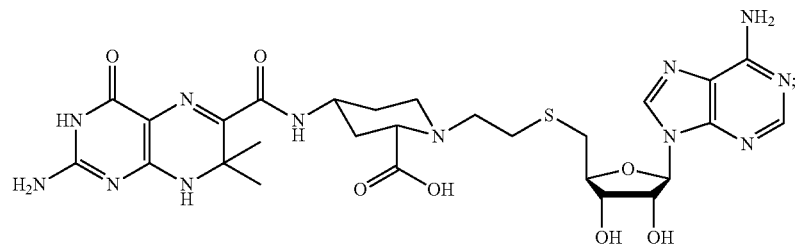

(102)

-continued
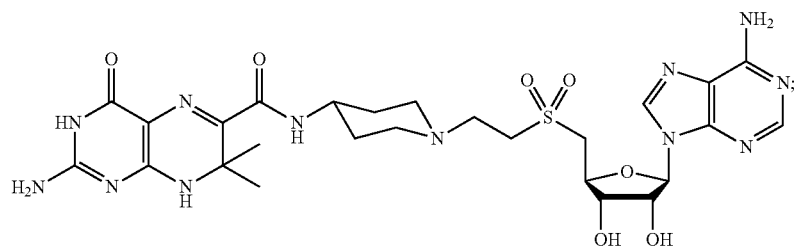
(103)
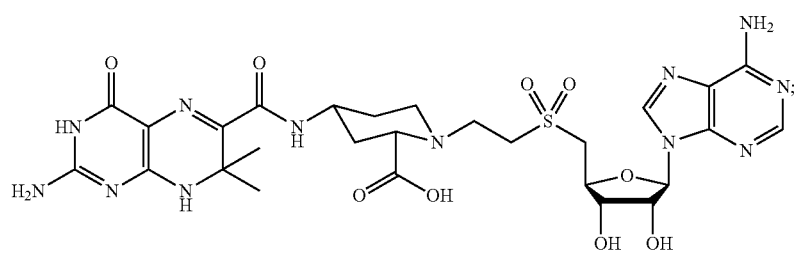
(104)
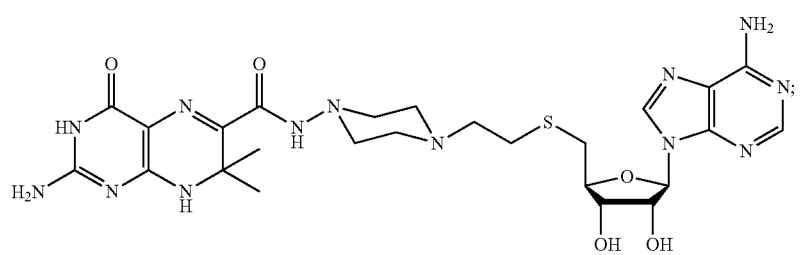
(105)
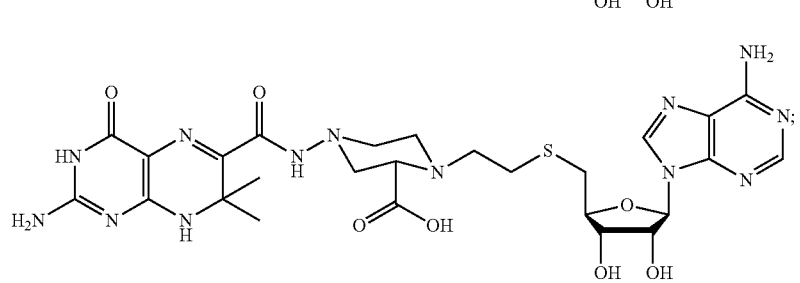
(106)
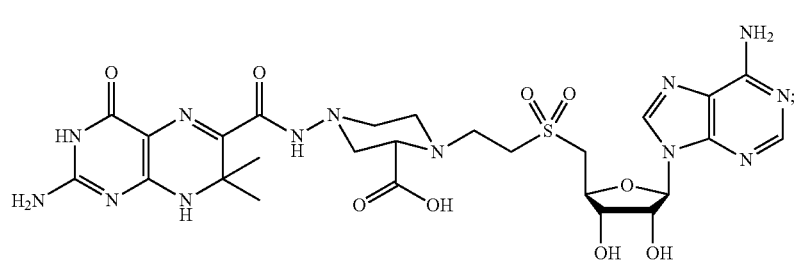
(107)
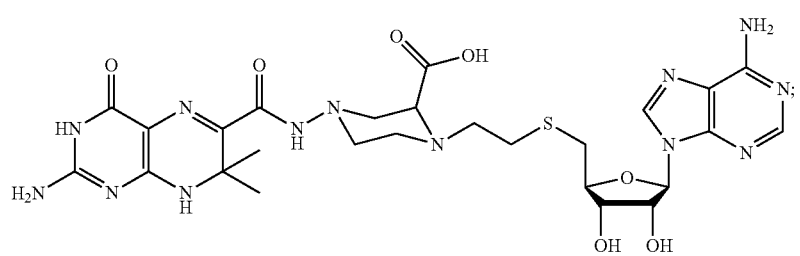
(108)

-continued
(109)
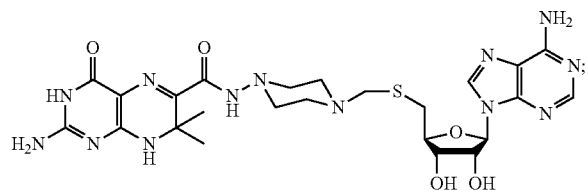
(110)
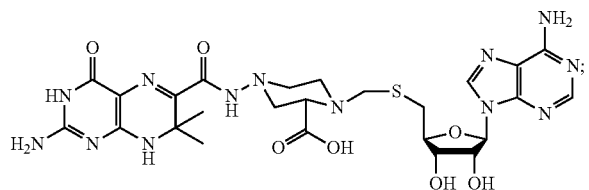
(111)
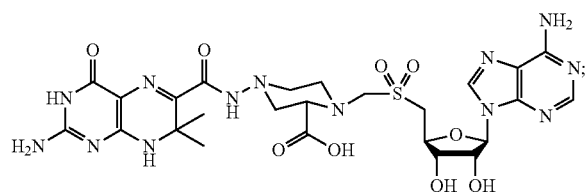
(112)
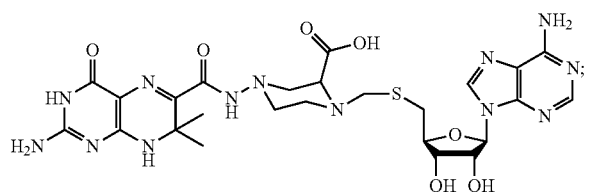
(113)
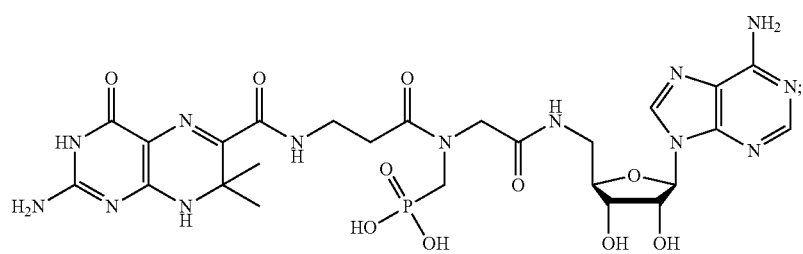
(114)
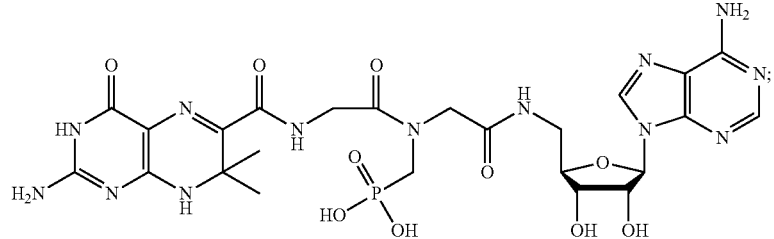
(115)
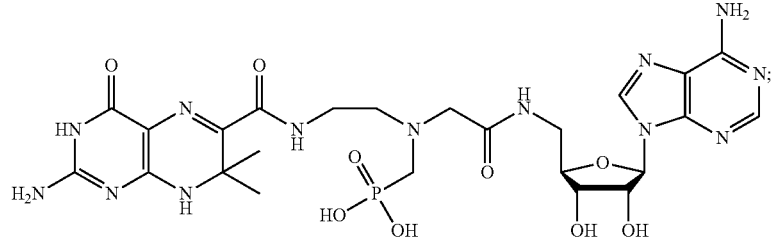
(116)
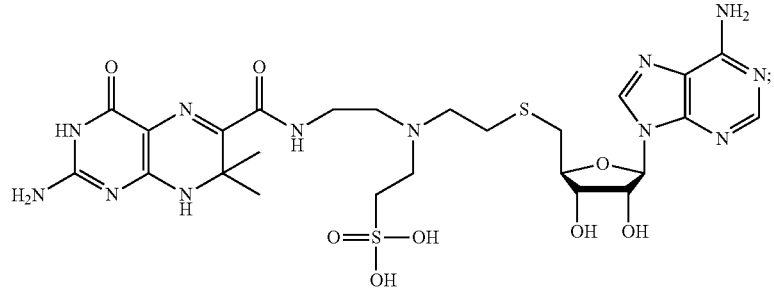

-continued
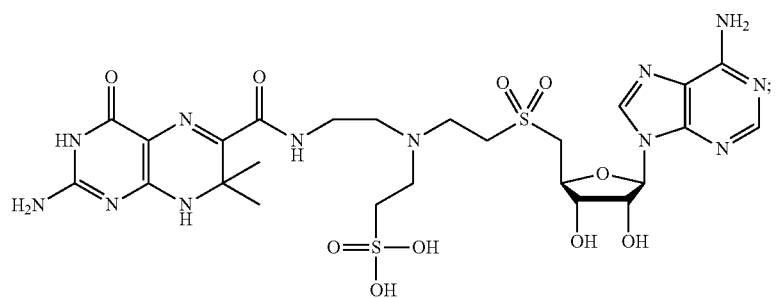
(117)
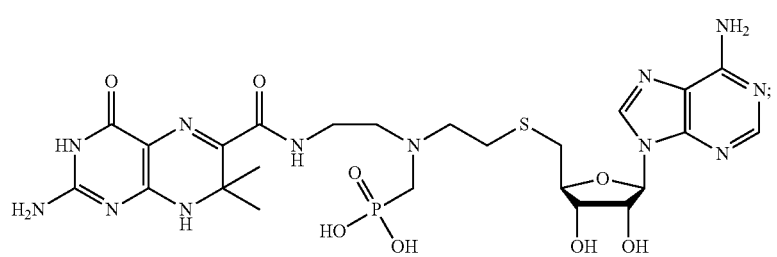
(118)
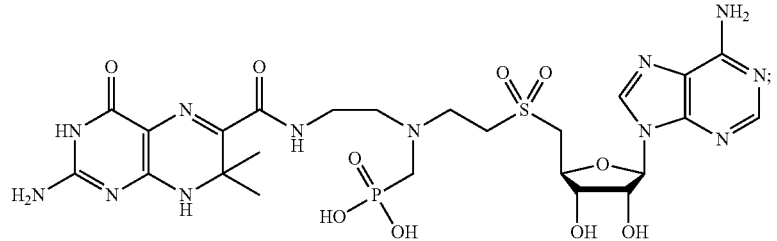
(119)
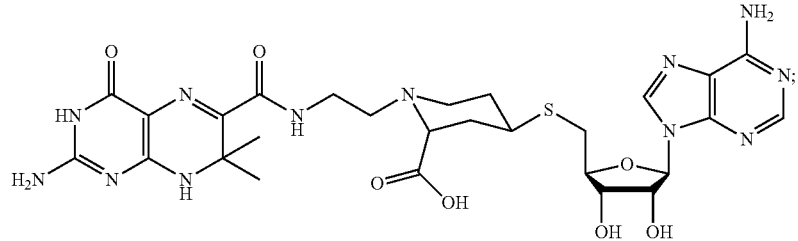
(120)
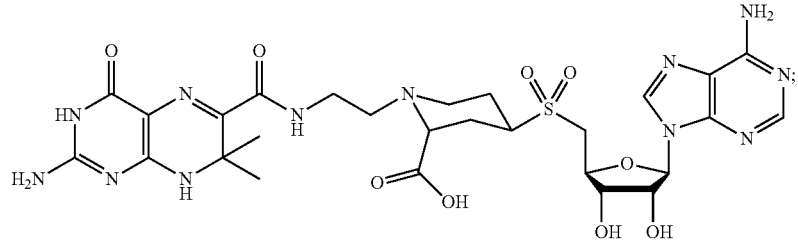
(121)
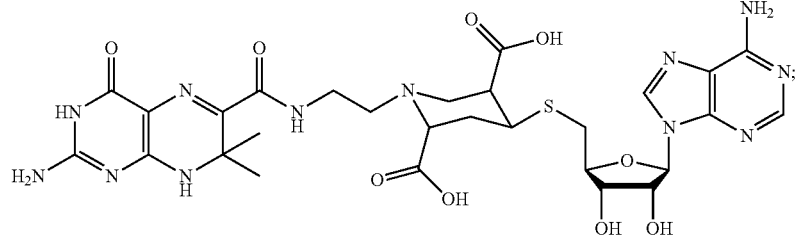
(122)

(123)
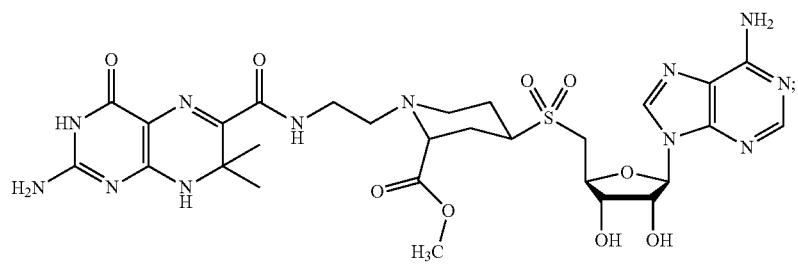
(124)
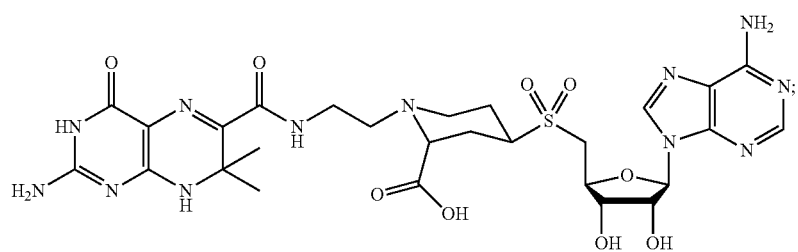
(125)
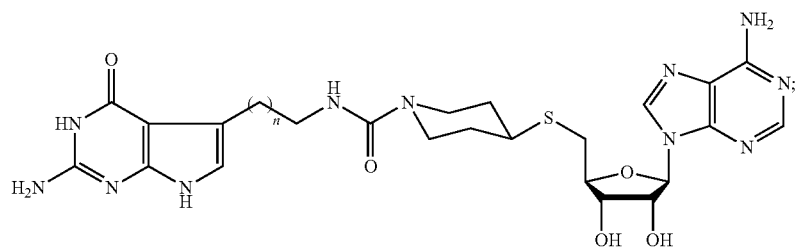
(n = 1 or 2)
(126)
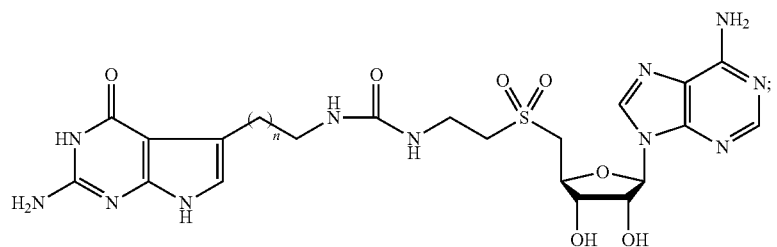
(n = 1 or 2)
(127)
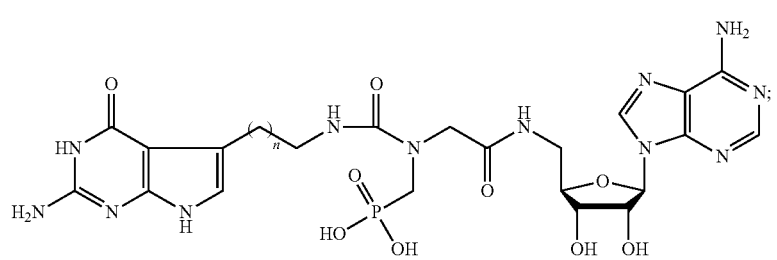
(n = 1 or 2)

-continued
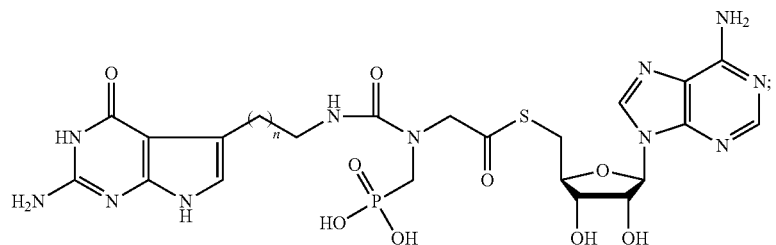
(128)
($n$ = 1 or 2)
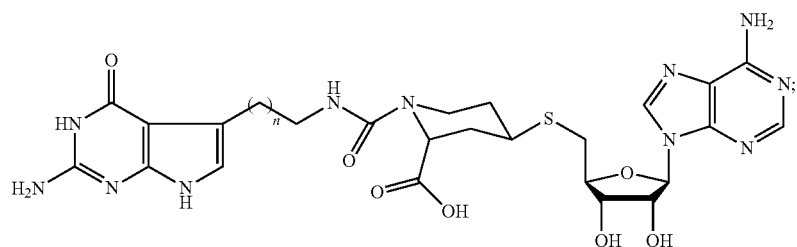
(129)
($n$ = 1 or 2)
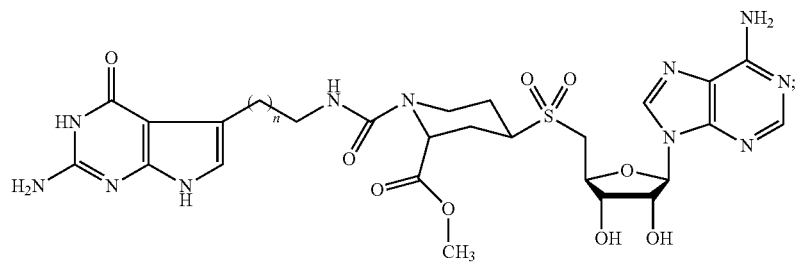
(130)
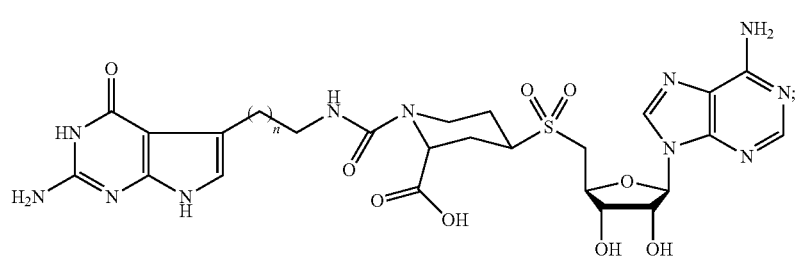
(131)
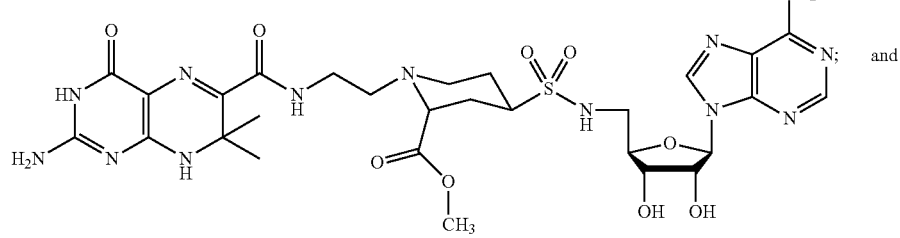
(132)
and
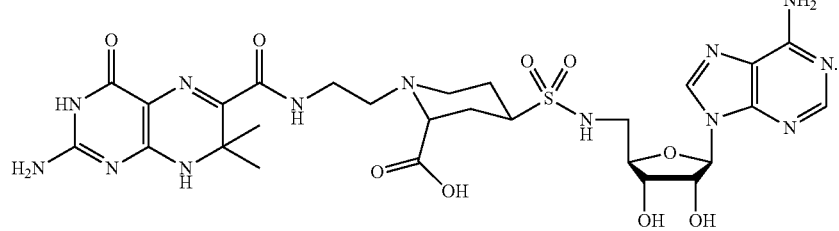
(133)

Figure 1B:
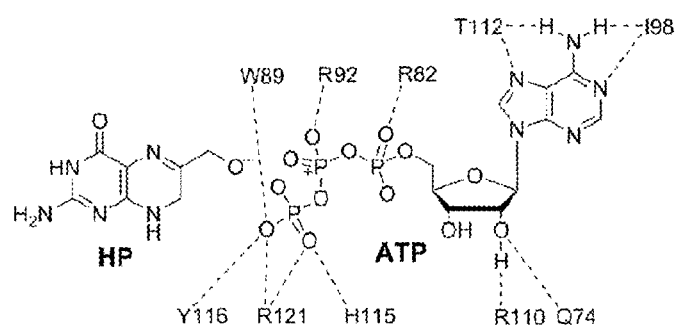
Figure 1C:
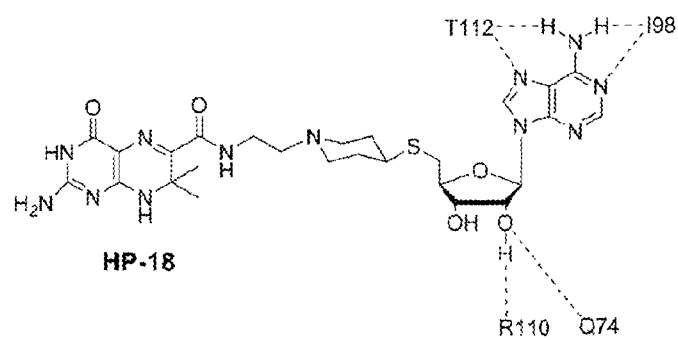
Figure 1D:
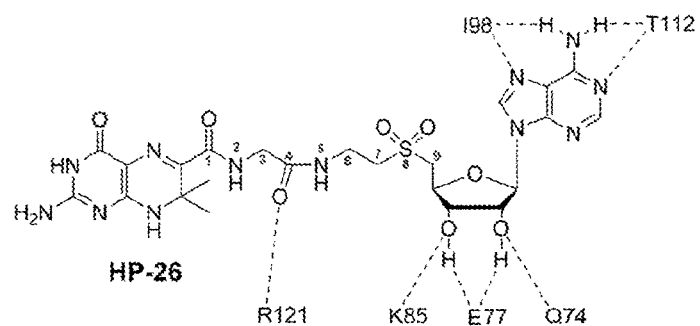

The pterin and adenosine moieties of the FIG. 1C and FIG. 1D compounds interact with HPPK in the same manner as these two moieties in HP and ATP except that the adenine ring of the FIG. 1D compound is flipped. As such, no further improvement is feasible regarding the pterin and purine moieties. We modified the linker such that it mimics the transition state of pyrophosphoryl transfer. Crystal structure analysis (data not shown) indicates that the triphosphate moiety of MgAMPCPP interacts with the side chains of R82, W89, R92, H115, Y116, and R121. Based on the FIG. 1D structure, a phosphate group was introduced to mimick the γ-phosphate group of ATP, leading to the design of new inhibitors, including Compound 114 and Compound 118, with different linkage properties.

The HPPK:Compound 114 crystal structure (not shown) contains 1 HPPK (residues 1-83, 91-158), 1 HP-39, and 227 water molecules in the asymmetric unit. As indicated, residues 84-90 are disordered. Residues R82 and R92 play dynamic roles in the catalytic cycle of the enzyme. Previous structures indicate that R92 first binds to the α-phosphate group of ATP and then shifts to interact with the β-phosphate as R82, which initially does not bind to ATP, moves in and binds to α-phosphate when the pyrophosphoryl transfer is about to occur. Between R82 and R92 is Loop 3 that is required for the assembly of the active center and essential for catalysis. The fact that Loop 3 is disordered in the HPPK:114 complex indicates that the protein and the inhibitor are not sufficiently complementary so that Loop 3 cannot settle down over and seal the active center as shown by previous structures in which Loop 3 residue W89 recognizes the γ phosphate of ATP.

The HPPK:Compound 118 structure (not shown) contains 2 HPPK (residues 1-158), compound 118, and 142 water molecules in the asymmetric unit. The two copies of the complex are virtually identical. Unlike the Loop 3 in the HPPK:Compound 114 structure, the Loop 3 in the HPPK:compound 118 complex is well defined and exhibits the open conformation, as in the HPPK. In the HPPK:compound 118 complex, the distance between W89 and the phosphate group of compound 118 is ~25 Å.

Figure 2A:
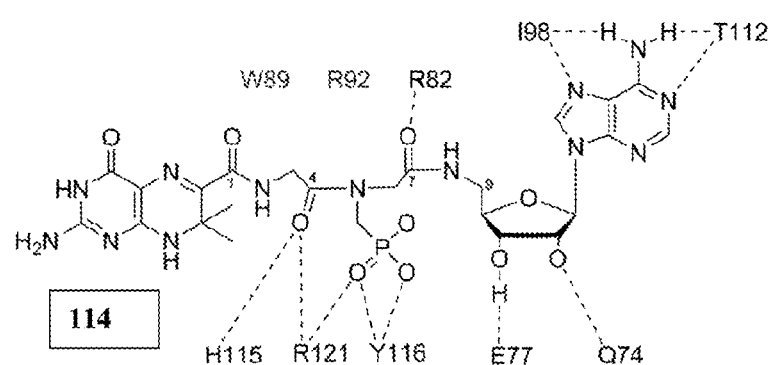
FIGS. 2A-B show new HPPK inhibitors.

In the HPPK:compound 114 complex, the adenine base is flipped (FIG. 2A), as observed previously in the HPPK:Inhibitor complex of FIG. 1D. These two inhibitors contain a common carbonyl group in position 4 of the linkage. In the HPPK:compound 114 complex, this carbonyl group forms two hydrogen bonds, one with R122 and the other with H115 (FIG. 2A). In the earlier HPPK:Inhibitor complex, this carbonyl group also forms a hydrogen bond with R122 (FIG. 1D), but forms a water-bridged hydrogen bond with H115 (not shown). It appears that this carbonyl-protein interaction dictates the downstream conformation of the linker, resulting in the flipped adenine base. Although the flipped adenine base forms the same number of hydrogen bonds as the unflipped base in the HPPK:MgAMPCPP:HP (FIG. 1B) and HPPK:Inhibitor (FIG. 1C) complexes, the fit between the flipped base and the binding site cannot be as good as the unflipped.

Figure 2B:
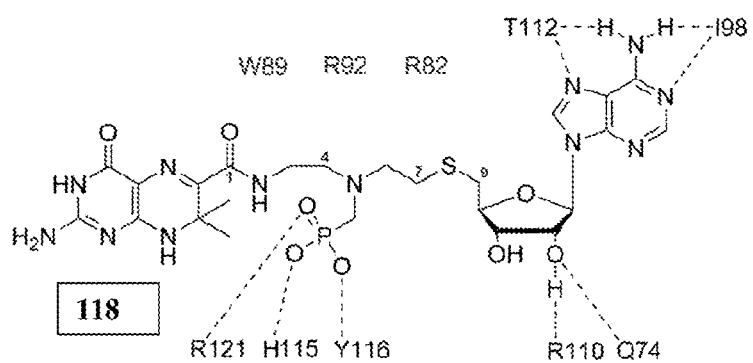

In addition to the carbonyl group at position 4, compound 114 contains a second carbonyl group at position 7 in the linker (FIG. 2A). In the HPPK:Compound 114 complex, a hydrogen bond is formed between R82 side chain and the carbonyl group at position 7. In the HPPK:Compound 118 complex, however, R82 and R92 do not interact with the inhibitor at all (FIG. 2B). The consequence of this difference is dramatic and surprising. The R82 and R92 side chains in the HPPK:114 complex are positioned similar to their counterparts in the HPPK:MgAMPCPP:HP complex. In contrast, these two arginine side chains in the HPPK:118 complex are not properly positioned and Loop 3 is completely open. Therefore, the structures suggest that the introduction of an electron-rich carbonyl and carboxylate group into linkage position 7 of 118 significantly changes the conformation of Loop 3 and thereby improve the potency of the inhibitor.

The affinities of 114 and 118 are significantly higher than previously known HPPK inhibitors, especially 118. It is the phosphate group in the two transition state mimetics that improves the protein-inhibitor interaction significantly by interacting with three more side chains that interact with ATP in the catalytic assembly of the enzyme (FIGS. 1B and 2). The flipped adenine ring system imposes a negative impact to the potency of the inhibitor.

Pharmaceutical Preparations

Compounds disclosed herein can be administered as the neat chemical, but are preferably administered as a pharmaceutical composition. Accordingly, pharmaceutical compositions comprising a compound or pharmaceutically acceptable salt of Formula I, together with at least one pharmaceutically acceptable carrier are provided herein. The pharmaceutical composition may contain a compound or salt of Formula I as the only active agent, or may contain one or more additional active agents.

Compounds disclosed herein may be administered orally, topically, intravenously, intramuscularly, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compounds described herein.

The pharmaceutical compositions can be formulated for oral administration. These compositions contain between 0.1 and 99 weight % (wt. %) of a purine pterin HPPK inhibitor of the disclosure and usually at least about 5 wt. % of a purine pterin HPPK inhibitor of the disclosure. Some embodiments contain from about 25 wt. % to about 50 wt. % or from about 5 wt. % to about 75 wt. % of the linked purine pterin HPPK inhibitor of the disclosure.

Compounds of this disclosure can also be formulated for intravenous administration. Intravenous formulations of the disclose purine pterin HPPK inhibitors can include one or more of a surface stabilizer (such as povidone or dextran), surfactant, preservative, pH adjuster, physiological saline, or sucrose. An injectable or intravenous formulation of this disclosure may include 0.25 mg/mL, 0.5 mg/mL, 1 mg/mL, 2 mg/mL, 5 mg/mL, 10 mg/mL, or 15 mg/ml of a purine pterin inhibitor of the disclosure.

Methods of Treatment

Methods of treating bacterial infections by providing an effective amount of a compound of the invention to a patient having a bacterial infection are provided. A compound as described herein may be provided as the only active agent or may be provided together with one or more additional active agents. Bacterial infections that may be treated with compounds of Formula I include, but are not limited to, Gram negative or Gram positive bacterial infections, including drug-resistant infections, *Escherichia coli, Acinobacter baumannii, Yersinia pestis, Clostridium difficile, Bacillus anthracis, Francisella tularensis, Klebsiella pneumonia, Staphylococcus aureus, Pseudomonas aeruginosa, Enterococcus faecalis, Enterococcus faecium, Mycobacterium tuberculosis*, ESKAPE pathogens (*Enterobacteria*), and *Helicobacter pylori* infections.

The pharmaceutical compositions disclosed herein are useful for treating bacterial infections in human and non-human patients. Non-human patients include, for example, livestock animals and companion animals.

An effective amount of a pharmaceutical composition as provided by this disclosure may be an amount sufficient to (a) cause a regression of the bacterial infection; or (b) cause a cure of a bacterial infection such that bacterial particles, or anti-bacterial antibodies, can no longer be detected in a previously infected patient's blood or plasma. An amount of a pharmaceutical composition needed to inhibit the progress or cause a regression of a bacterial infection, includes an amount effective to stop the worsening of symptoms of the infection or reduce the symptoms experienced by an infected patient. Alternatively a halt in progression or regression of infections may be indicated by any of several markers for the disease. For example, a lack of increase or reduction in the number of bacterial particles in the patient's blood or serum, or a lack of increase or reduction in the number of circulating anti-bacterial antibodies in a patient's blood, or return to normal for the patient's white blood cell count are markers of a halt in progression or regression of bacterial infection.

An effective amount of a combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

Methods of treatment include providing certain dosage amounts of a compound of Formula I to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the patient treated and the particular mode of administration.

In certain embodiments 25 mg to 500 mg, or 25 mg to 200 mg of a compound of Formula I are provided daily to a patient. Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, age, body weight, general health, sex, diet, time of administration, route of administration, rate of excretion, drug combination, and the severity of the particular disease in the patient undergoing therapy.

Combination Methods

Pharmaceutical compositions and methods of treatment in which a compound or salt of Formula I is provided together with one or more additional active agents are included herein. In certain embodiments the active agent (or agents) is an anti-bacterial compound such as an antibiotic. The compound of Formula I and an additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods disclosed herein comprise administering or delivering the compound of Formula I and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

EXAMPLES

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, may also be used in the synthetic schemes and examples.

DCM Dichloromethane
DIAD Diisopropyl azodicarboxylate
DIPEA N,N-Diisopropylethylamine
DMF Dimethyl formamide
EtOH Ethanol
HATU (1-[Bis(dimethylamino)methylene]-1H-1,2,3-triazolo[4,5-b]pyridinium oxid hexafluorophosphate)
HP 6-hydroxymethyl-7,8-dihydropterin
HPPK 6-hydroxymethyl-7,8-dihydropterin pyrophosphokinase
NBS N-bromosuccinamide
TFA trifluoroacetic acid
TMS Trimethylsilane
T-HYDRO t-butyl hydroperoxide General Experimental Information The compound 2',3'-isopropylideneadenosine (1, Scheme 1) was purchased from TCI America. All other chemicals were purchased from Sigma-Aldrich. Starting materials and solvents were used without further purification. Anhydrous reactions were conducted under a positive pressure of dry $N_2$. Reactions were monitored by thin layer chromatography (TLC) on Baker-flex Silica Gel IB-F (J. T. Baker). Final compounds and intermediates were purified by flash chromatography performed on Teledyne ISCO Combiflash Rf system using RediSep Rf columns. Ion exchange chromatography was performed using strata Scx (50 μm particle size, 70 Å pore) resin cartridges. Preparative high pressure liquid chromatography (HPLC) was conducted using a Waters 600E system using a Waters 2487 dual λ absorbance detector and Phenomenex $C_{18}$ columns (250 mm×21.2 mm, 5 μm particle size, 110 Å pore) at a flow rate of 10 mL/min. A binary solvent systems consisting of A=0.1% aqueous TFA and B=0.1% TFA in acetonitrile was employed with the gradients as indicated. $^1H$ and $^{13}C$ NMR data were obtained on a Varian 400 MHz spectrometer and are reported in ppm relative to TMS and referenced to the solvent in which the spectra were collected. Mass spectra were measured with Agilent 1100 series LC/Mass Selective Detector, Agilent 1200 LC/MSD-SL system and Thermoquest Surveyor Finnigan LCQ deca. All compounds tested were at least 95% pure by LCMS and NMR.

Example 1

Synthesis of 2-amino-7,7-dimethyl-4-oxo-3,4,7,8-tetrahydro-pteridine-6-carbaldehyde (Compound 12)

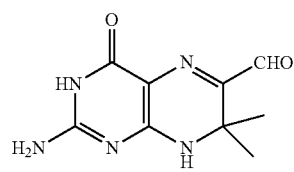

Intermediate Compounds 11 and 12 are prepared according to the procedure shown in Reaction Scheme I.

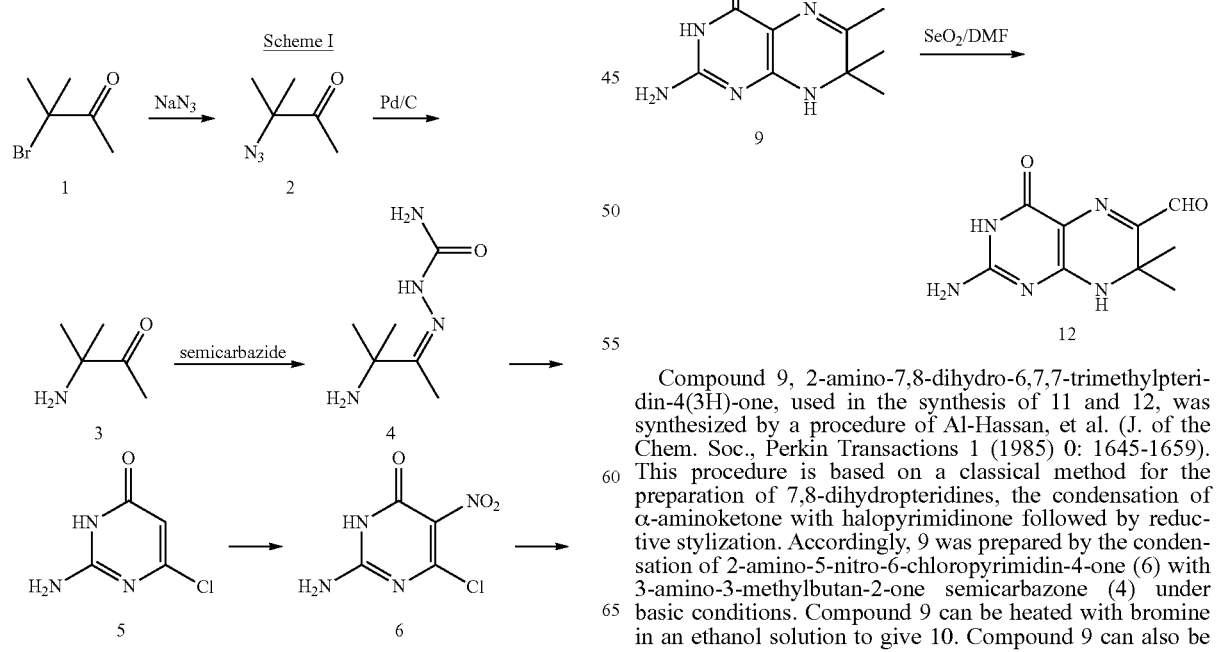

Compound 9, 2-amino-7,8-dihydro-6,7,7-trimethylpteridin-4(3H)-one, used in the synthesis of 11 and 12, was synthesized by a procedure of Al-Hassan, et al. (J. of the Chem. Soc., Perkin Transactions 1 (1985) 0: 1645-1659). This procedure is based on a classical method for the preparation of 7,8-dihydropteridines, the condensation of α-aminoketone with halopyrimidinone followed by reductive stylization. Accordingly, 9 was prepared by the condensation of 2-amino-5-nitro-6-chloropyrimidin-4-one (6) with 3-amino-3-methylbutan-2-one semicarbazone (4) under basic conditions. Compound 9 can be heated with bromine in an ethanol solution to give 10. Compound 9 can also be oxidized by $SeO_2$ in DMF to give 12.

Synthesis of Compound 12

Compounds 10, 11, and 12 (Scheme 1) are intermediates useful in the preparation of compounds of Formula I. To synthesize 12, a solution of 9 (207 mg, 1.0 mmol) in DMF (10 mL) and pyridine (105 uL, 1.30 mmol) was treated with $SeO_2$ (145 mg, 1.30 mmol) and stirred at room temperature for 5 h. The reaction was then heated to 80° C. for 15 min. The solvent was evaporated under high vacuum and the residue purified by flash chromatography (silica gel, methanol:dichloromerhane=2:8) to give 12 (199 mg, 0.9 mmol, 90%) as a yellowish powder. MS (ESI) calculated for $C9H11N5O2$ [M+H]+ 222.09, found 222.1.

Example 2

Synthesis of Compound 101

Compound 101, 2-amino-N-(1-(2-((((2S,3S,4R,5R)-5-(6-amino-9H-purin-9-yl)-3,4-dihydroxytetrahydrofuran-2-yl)methyl)thio)ethyl)piperidin-4-yl)-7,7-dimethyl-4-oxo-3,4,7,8-tetrahydropteridine-6-carboxamide, was prepared according to the Reaction Scheme II process.

A mixture of triphenylphosphine and diisopropyl azodicarboxylate in tetrahydrofuran was added to a mixture of tert-butyl (1-(2-hydroxyethyl)piperidin-4-yl)carbamate (13) and thioacetic acid in tetrahydrofuran to afford S-(2-(4-((tert-butoxycarbonyl)amino)piperidin-1-yl)ethyl) ethanethioate (14). Compound 12 was reacted with sodium methoxide to form the thiol, followed by the reaction with chloroadenosine to give tert-butyl (1-(2-((((2S,3S,4R,5R)-5-(6-amino-9H-purin-9-yl)-3,4-dihydroxytetrahydrofuran-2-yl)methyl)thio)ethyl)piperidin-4-yl)carbamate (15). The BOC group was removed by TFA, yielding (2R,3R,4S,5S)-2-(6-amino-9H-purin-9-yl)-5-(((2-(4-aminopiperidin-1-yl)ethyl)thio)methyl)tetrahydrofuran-3,4-diol (16). Compound 16 was linked to 2-amino-7,7-dimethyl-4-oxo-3,4,7,8-tetrahydro-pteridine-6-carboxylic acid using coupling reagent HATU to give final product 2-amino-N-(1-(2-((((2S,3S,4R,5R)-5-(6-amino-9H-purin-9-yl)-3,4-dihydroxytetrahydrofuran-2-yl)methyl)thio)ethyl)piperidin-4-yl)-7,7-dimethyl-4-oxo-3,4,7,8-tetrahydropteridine-6-carboxamide (101). Crystal structure of 101 in complex with *Escherichia coli* HPPK was determined at 1.83-Å resolution (structure not shown).

Scheme II

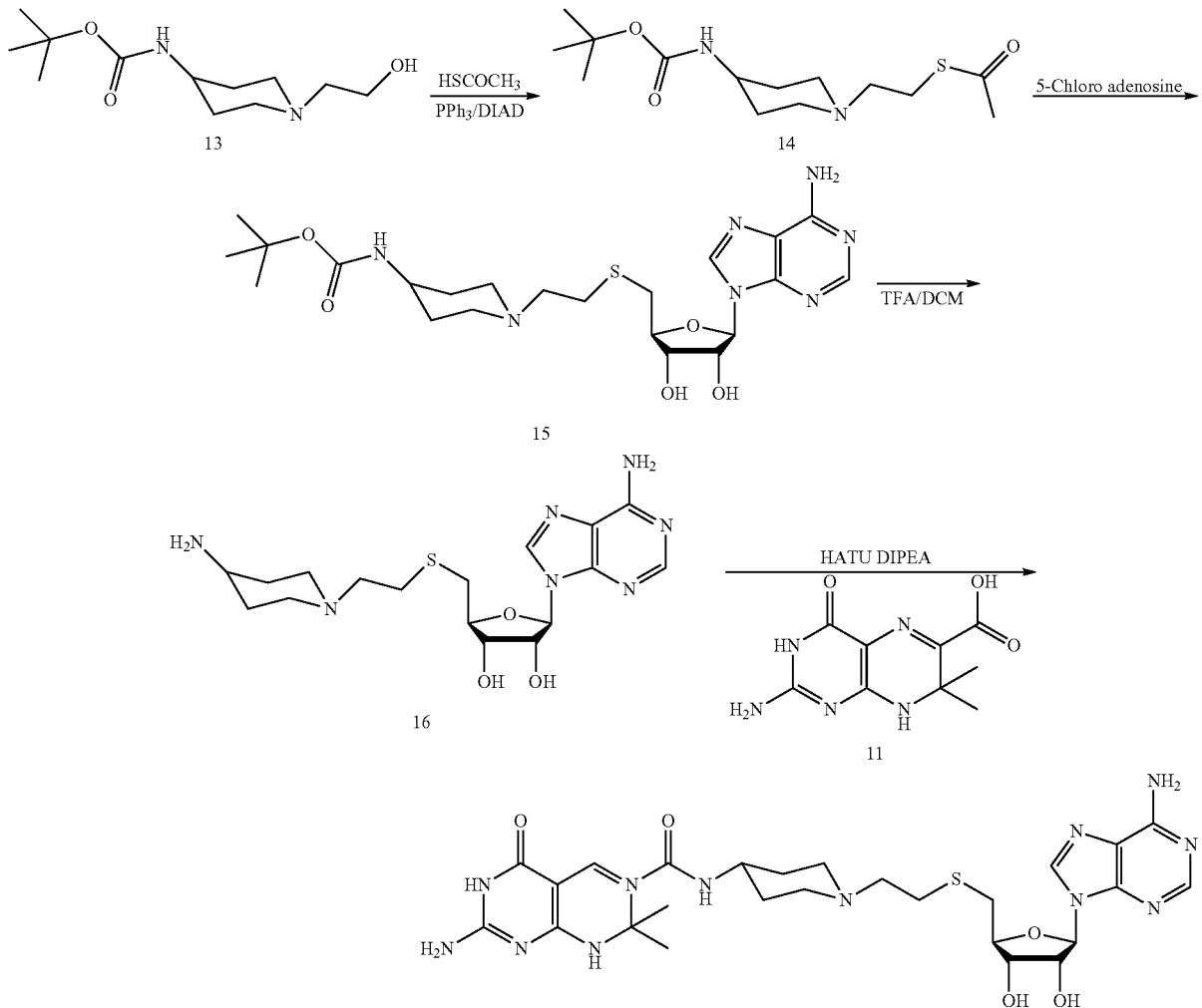

Compound 101

Example 3
Synthesis of Compound 118
Compound 118, (((2-(2-amino-7,7-dimethyl-4-oxo-3,4,7,8-tetrahydropteridine-6-carboxamido)ethyl)(2-(((((2S,3S,4R,5R)-5-(6-amino-9H-purin-9-yl)-3,4-dihydroxytetrahydrofuran-2-yl)methyl)thio)ethyl)amino)methyl)phosphonic acid, was prepared according to the process shown in Reaction Scheme III.
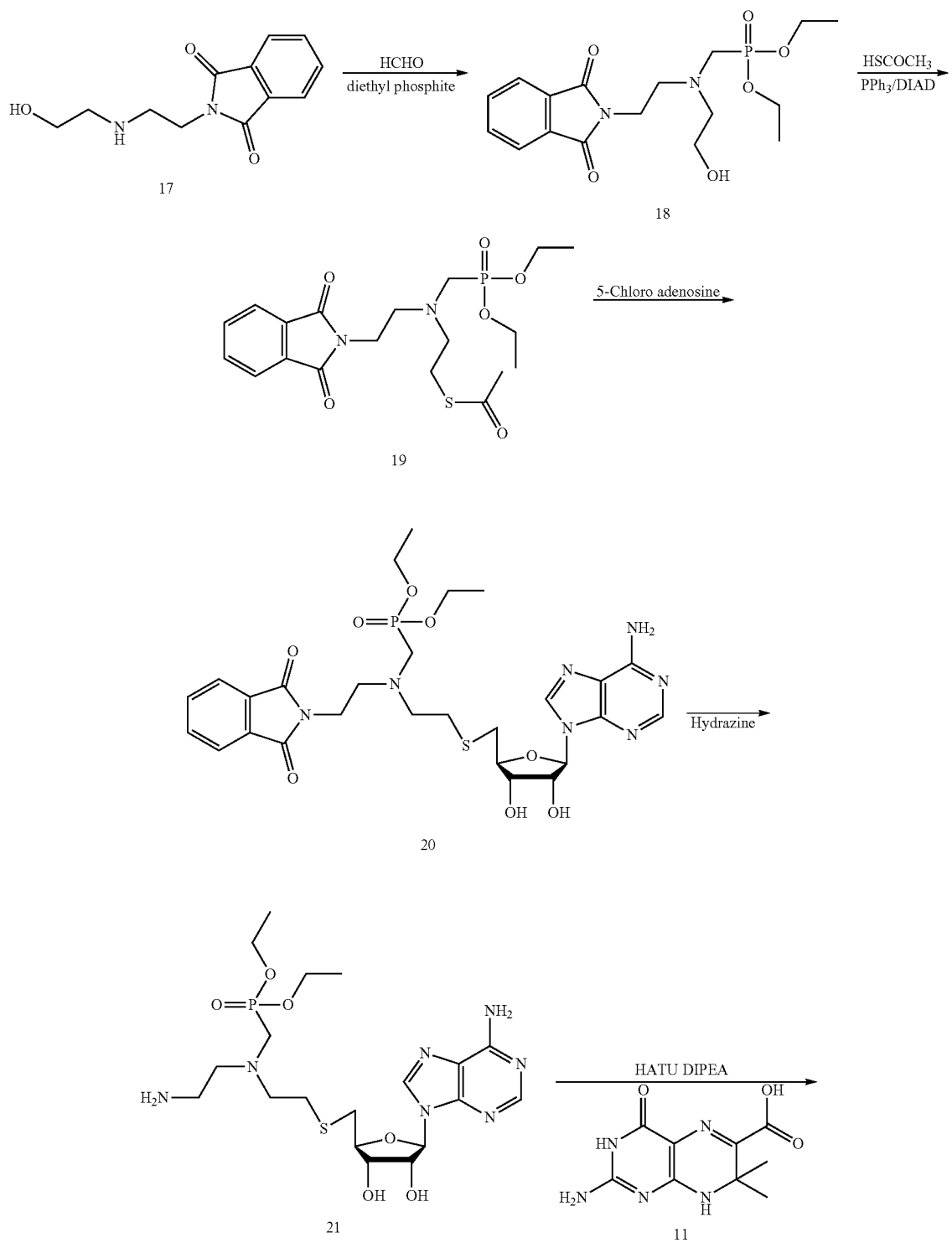

-continued

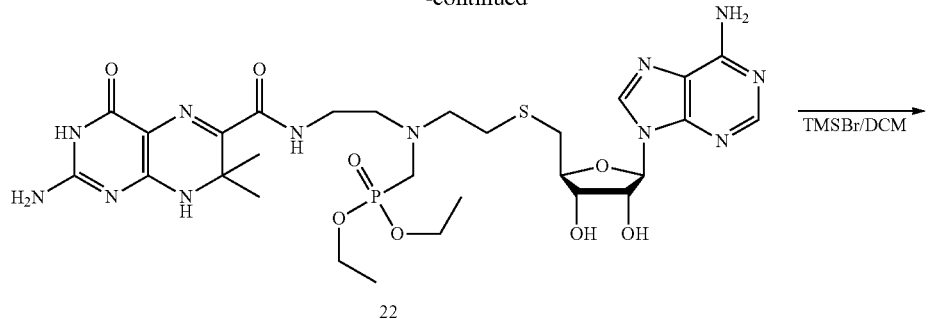

22

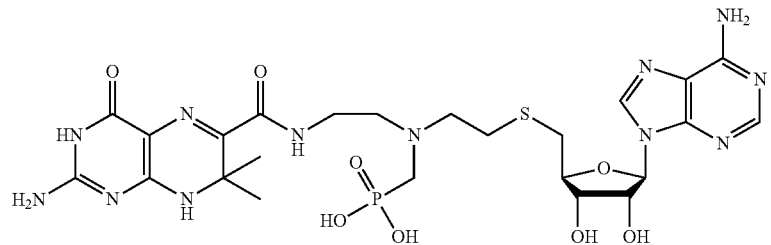

Compound 118

2-(2-((2-hydroxyethyl)amino)ethyl)isoindoline-1,3-dione (17) reacts with formalin and diethyl phosphite to give diethyl (((2-(1,3-dioxoisoindolin-2-yl)ethyl)(2-hydroxyethyl)amino)methyl)phosphonate (18). The Mitsunobu reaction between Compound 2 and thioacetic acid yielded S-(2-(((diethoxyphosphoryl)methyl)(2-(1,3-dioxoisoindolin-2-yl)ethyl)amino)ethyl) ethanethioate (19). Compound 3 reacted with sodium methoxide to form the thiol, followed by reaction with chloroadenosine to give diethyl (((2-((((2S,3S,4R,5R)-5-(6-amino-9H-purin-9-yl)-3,4-dihydroxytetrahydrofuran-2-yl)methyl)thio)ethyl)(2-(1,3-dioxoisoindolin-2-yl)ethyl)amino)methyl)phosphonate (20). Hydrazine was used to remove compound the phthalimide group on (4) to give diethyl (((2-((((2S,3S,4R,5R)-5-(6-amino-9H-purin-9-yl)-3,4-dihydroxytetrahydrofuran-2-yl)methyl)thio)ethyl)(2-aminoethyl)amino)methyl)phosphonate (21) Compound 5 was coupled with 2-amino-7,7-dimethyl-4-oxo-3,4,7,8-tetrahydro-pteridine-6-carboxylic acid using HATU to give diethyl (((2-(2-amino-7,7-dimethyl-4-oxo-3,4,7,8-tetrahydropteridine-6-carboxamido)ethyl)(2-((((2S,3S,4R,5R)-5-(6-amino-9H-purin-9-yl)-3,4-dihydroxytetrahydrofuran-2-yl)methyl)thio)ethyl)amino)methyl)phosphonate (22). TMSBr in DCM solution was used to remove the ethyl group of compound 6 to give the final product (((2-(2-amino-7,7-dimethyl-4-oxo-3,4,7,8-tetrahydropteridine-6-carboxamido)ethyl)(2-((((2S,3S,4R,5R)-5-(6-amino-9H-purin-9-yl)-3,4-dihydroxytetrahydrofuran-2-yl)methyl)thio) ethyl)amino)methyl)phosphonic acid (Compound 118). Crystal structure of 118 in complex with *Escherichia coli* HPPK was determined at 2.30-Å resolution (structure not shown).

Example 4

Synthesis of Compound 120

Compound 120, (2R,4R)-1-(2-(2-amino-7,7-dimethyl-4-oxo-3,4,7,8-tetrahydropteridine-6-carboxamido)ethyl)-4-((((2S,3S,4R,5R)-5-(6-amino-9H-purin-9-yl)-3,4-dihydroxytetrahydrofuran-2-yl)methyl)thio)piperidine-2-carboxylic acid, was prepared according the process shown in Reaction Scheme IV.

Scheme IV

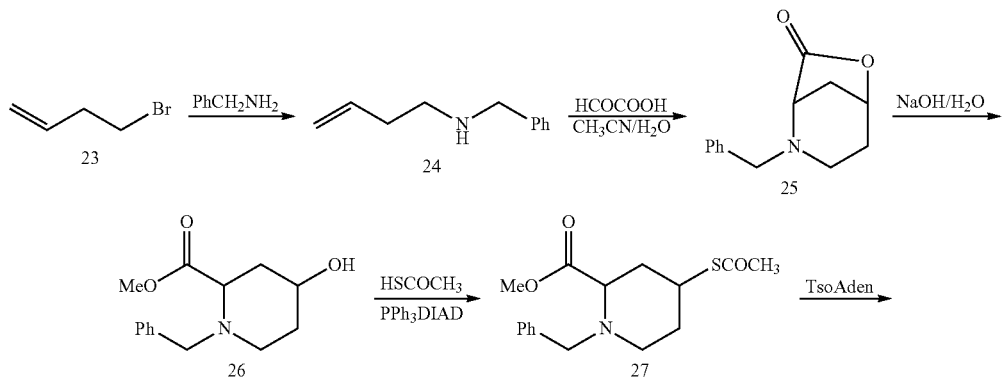

-continued
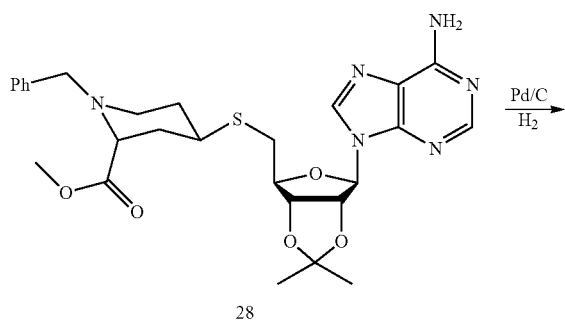
28
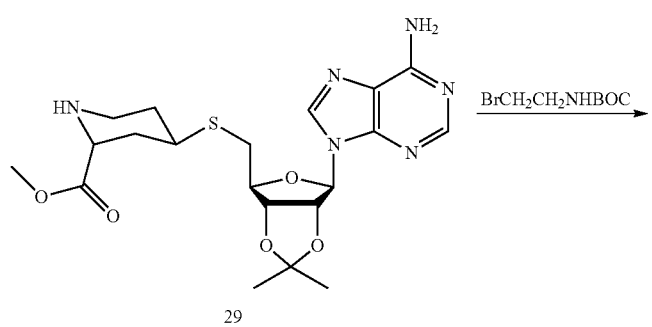
29
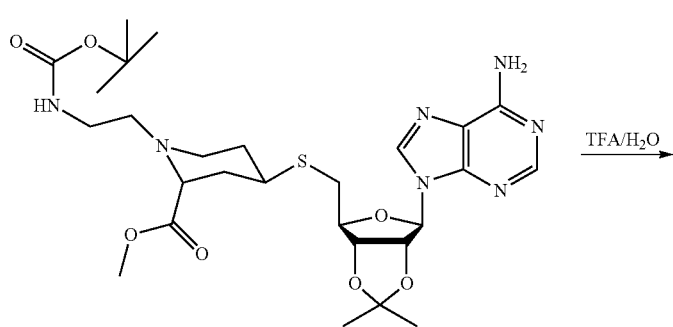
30
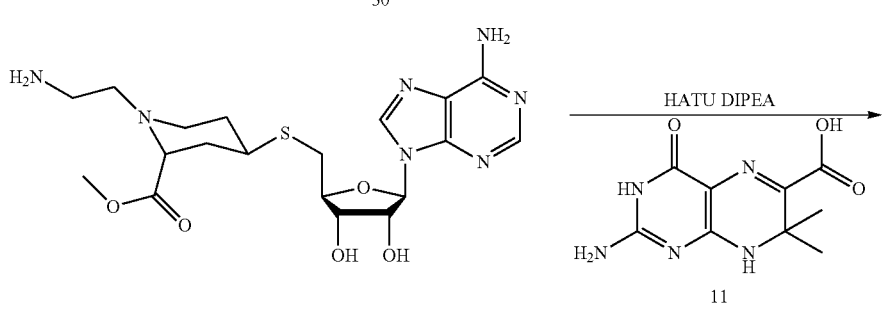
31
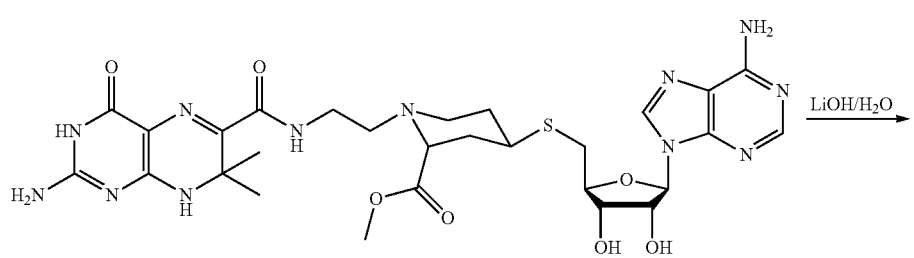
32

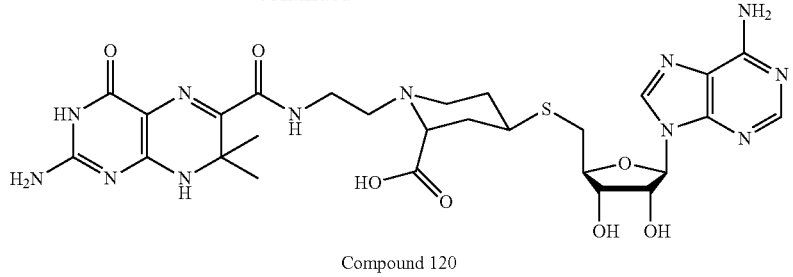

Compound 120

Reacting from 4-bromobut-1-ene (23) reacting with benzylamine in ethanol gives N-3-butenylbenzenemethanamine (24). When compound 24 is treated with glyoxylic acid in aqueous acetonitrile, lactone 2-benzyl-6-oxa-2-azabicyclo[3.2.1]octan-7-one (25) is isolated as the sole reaction product. Hydrolysis with 1M NaOH gives 1-benzyl-4-hydroxypiperidine-2-carboxylic acid (26). The resulting mixture of triphenylphosphine in tetrahydrofuran and diisopropyl azodicarboxylate in tetrahydrofuran was added to 26 and thioacetic acid in tetrahydrofuran to afford methyl 4-(acetylthio)-1-benzylpiperidine-2-carboxylate (27). Compound 27 reacts with sodium methoxide to form the thiol, followed by the reaction with 2',3'-O-isopropylidene-5'-O-toluene-p-sulfonyl adenosine to give methyl (2R,4R)-4-((((3aS,4S,6R,6aR)-6-(6-amino-9H-purin-9-yl)-2,2-dimethyltetrahydrofuro[3,4-d][1,3]dioxol-4-yl)methyl)thio)-1-benzylpiperidine-2-carboxylate (28). The benzyl group was removed by hydrogenation under Pd/C catalysis, yielding methyl (2R,4R)-4-((((3aS,4S,6R,6aR)-6-(6-amino-9H-purin-9-yl)-2,2-dimethyltetrahydrofuro[3,4-d][1,3]dioxol-4-yl)methyl)thio)piperidine-2-carboxylate (29). The subsequent reaction of compound 29 with (2-bromo-ethyl)-carbamic acid tert-butyl ester provided the key intermediate methyl (2R,4R)-4-((((3aS,4S,6R,6aR)-6-(6-amino-9H-purin-9-yl)-2,2-dimethyltetrahydrofuro[3,4-d][1,3]dioxol-4-yl)methyl)thio)-1-(2-((tert-butoxycarbonyl)amino)ethyl)piperidine-2-carboxylate (30). Under TFA/DCM conditions, cleavage of the BOC protection group yielded methyl (2R,4R)-1-(2-(12-azanyl)ethyl)-4-((((2S,3S,4R,5R)-5-(6-amino-9H-purin-9-yl)-3,4-dihydroxytetrahydrofuran-2-yl)methyl)thio)piperidine-2-carboxylate (31) that contained an amino group that would be used to link compound 31 to 2-amino-7,7-dimethyl-4-oxo-3,4,7,8-tetrahydro-pteridine-6-carboxylic acid (11) using the coupling reagent HATU to give methyl (2R,4R)-1-(2-(2-amino-7,7-dimethyl-4-oxo-3,4,7,8-tetrahydropteridine-6-carboxamido)ethyl)-4-((((2S,3S,4R,5R)-5-(6-amino-9H-purin-9-yl)-3,4-dihydroxytetrahydrofuran-2-yl)methypthio)piperidine-2-carboxylate (32). Compound 32 was hydrolyzed by 1 M lithium hydroxide solution to give the final product (2R,4R)-1-(2-(2-amino-7,7-dimethyl-4-oxo-3,4,7,8-tetrahydropteridine-6-carboxamido)ethyl)-4-((((2S,3S,4R,5R)-5-(6-amino-9H-purin-9-yl)-3,4-dihydroxytetrahydrofuran-2-yl)methyl)thio)piperidine-2-carboxylic acid (Compound 120). Crystal structure of 120 in complex with *Escherichia coli* HPPK was determined at 1.60-Å resolution (structure not shown).

Example 5

Synthesis of Compound 121

Compound 121 is prepared according to the synthetic scheme V, below.

Scheme V

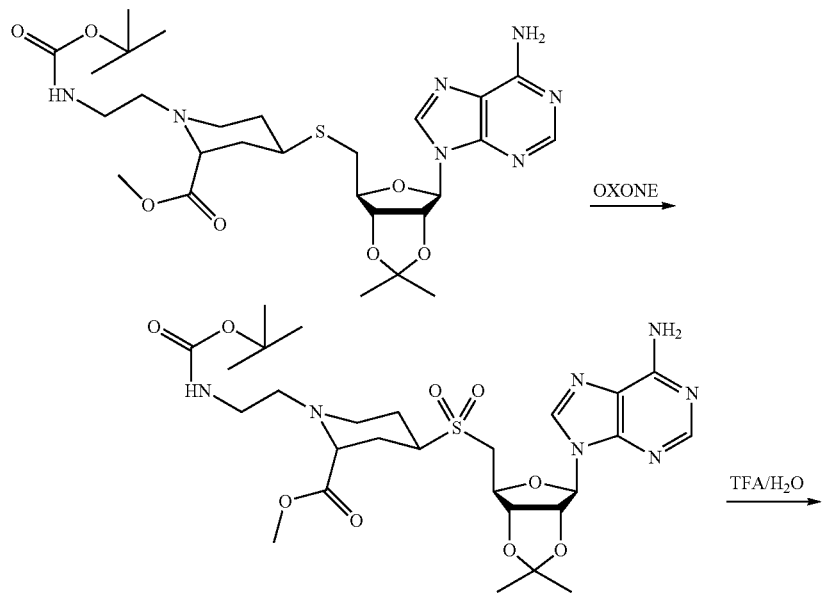

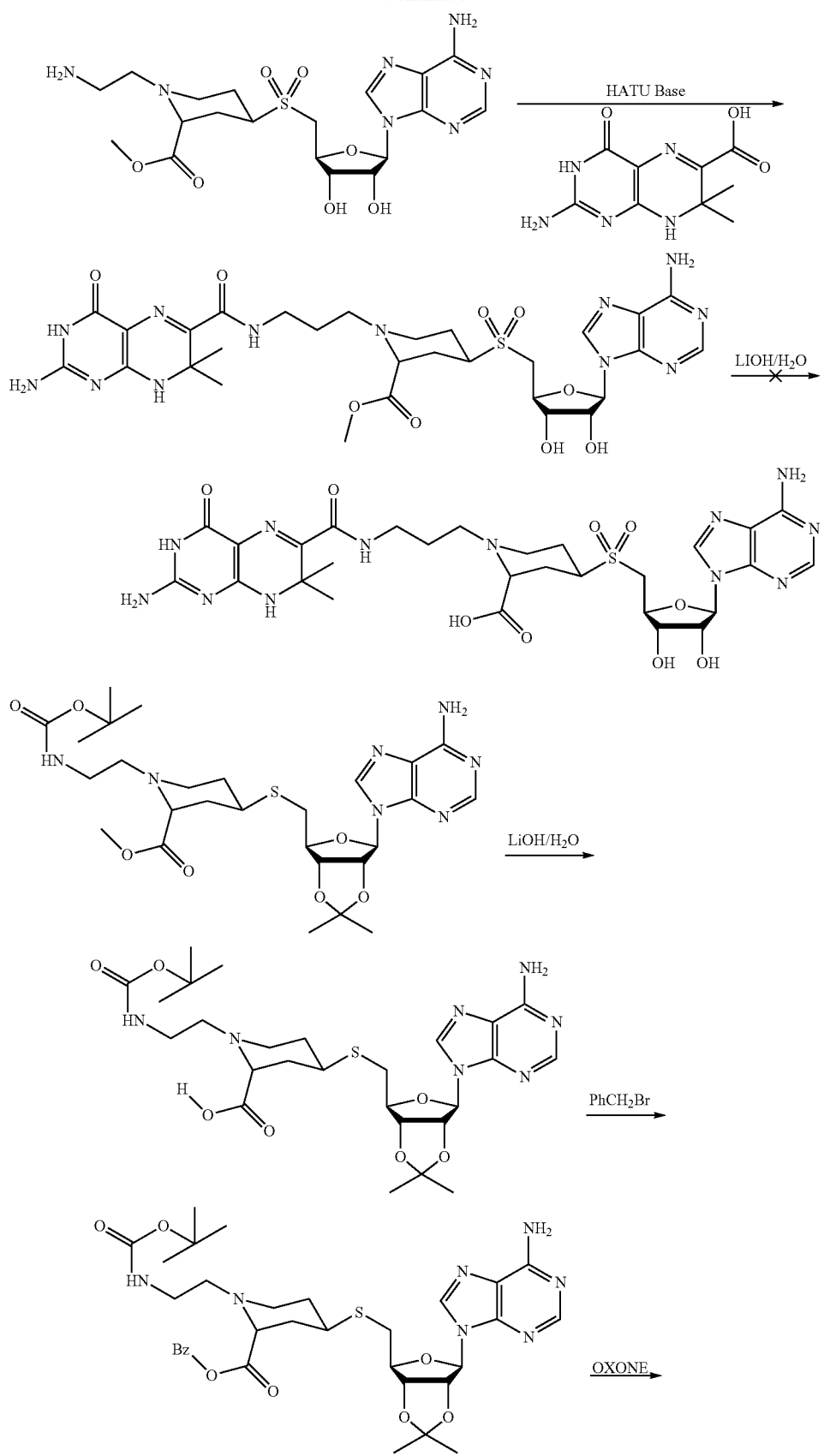

-continued
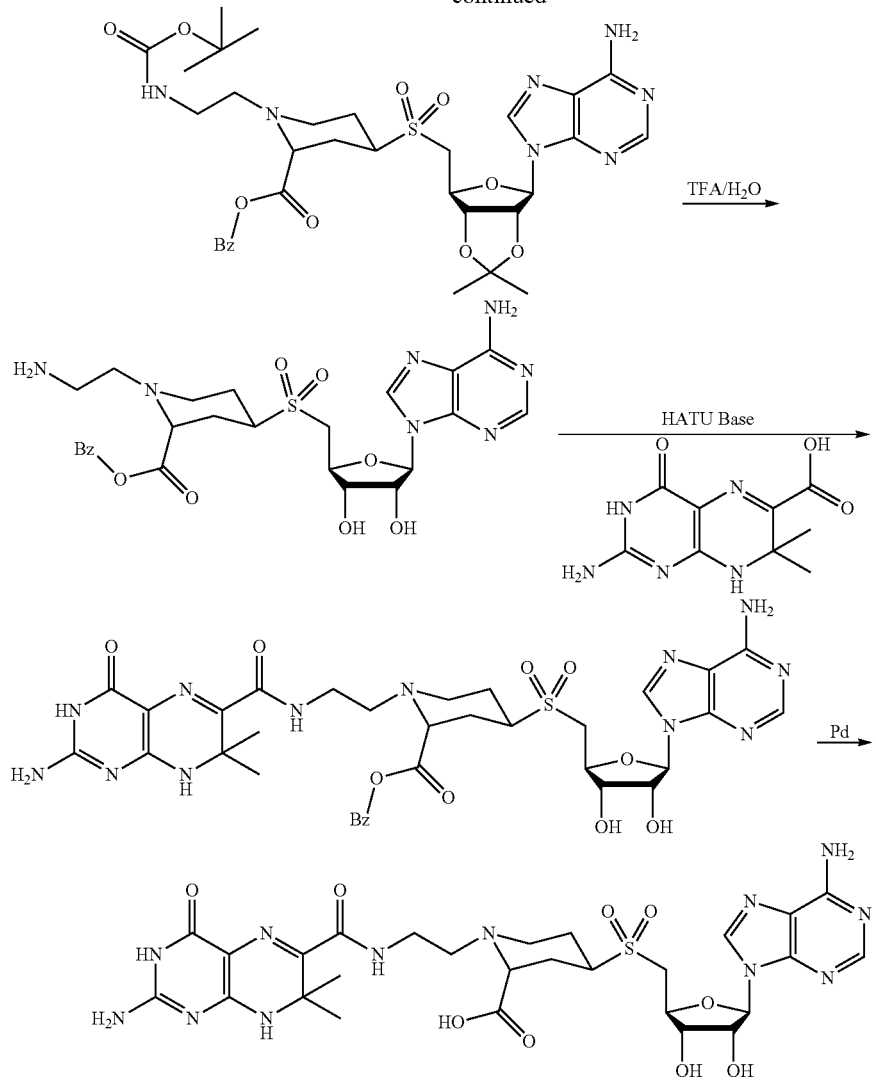
Example 6
Synthesis of Compound 132
Compound 132 is prepared according to the synthetic Scheme VI, below.
Scheme VI
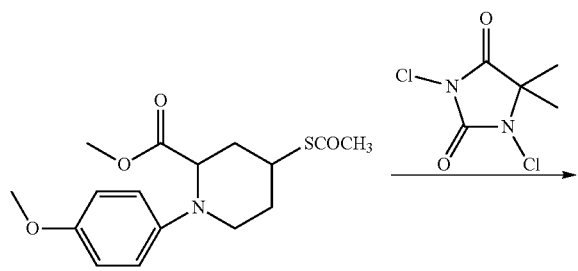

-continued
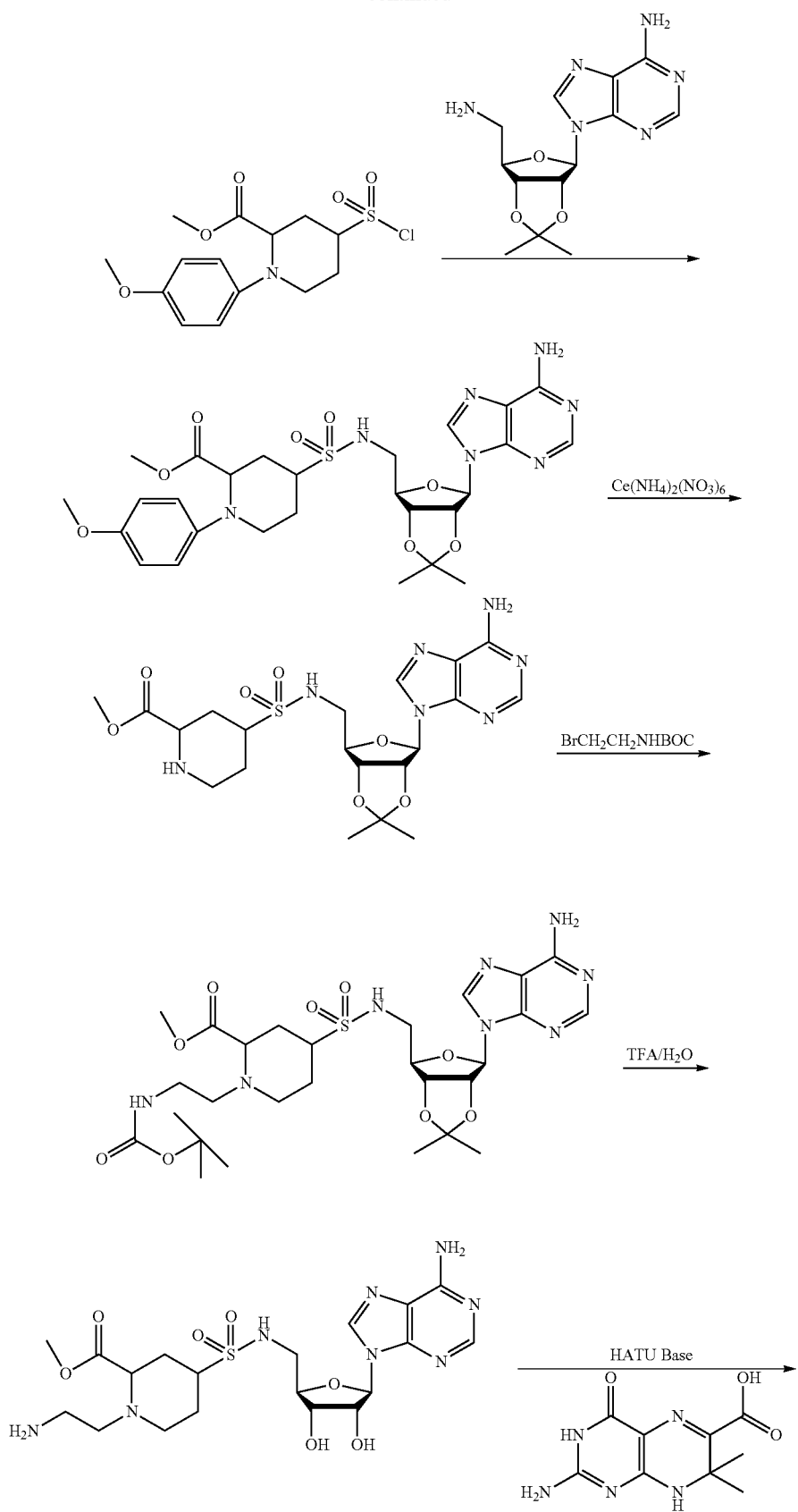

-continued
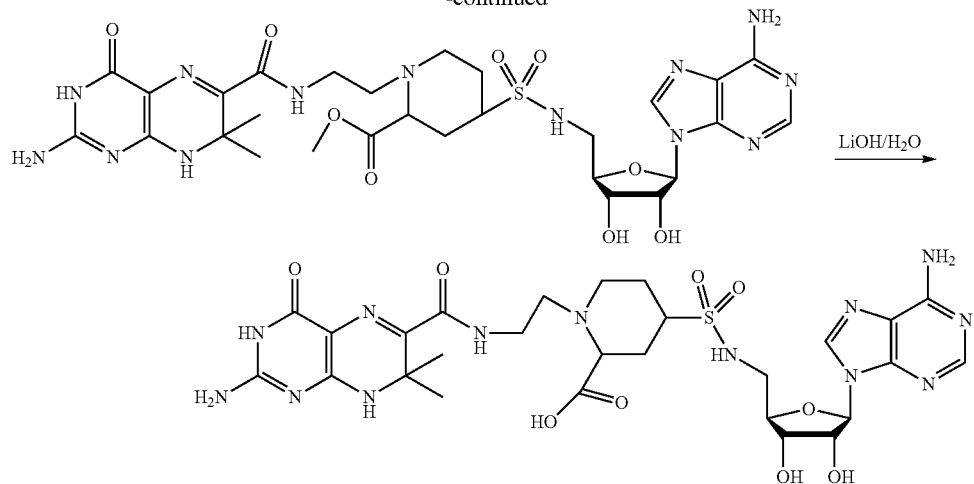
Example 7
Synthesis of Compounds 125 and 126
Compound 125 and 126 are prepared according to the synthetic Scheme VII, below.
Scheme VII
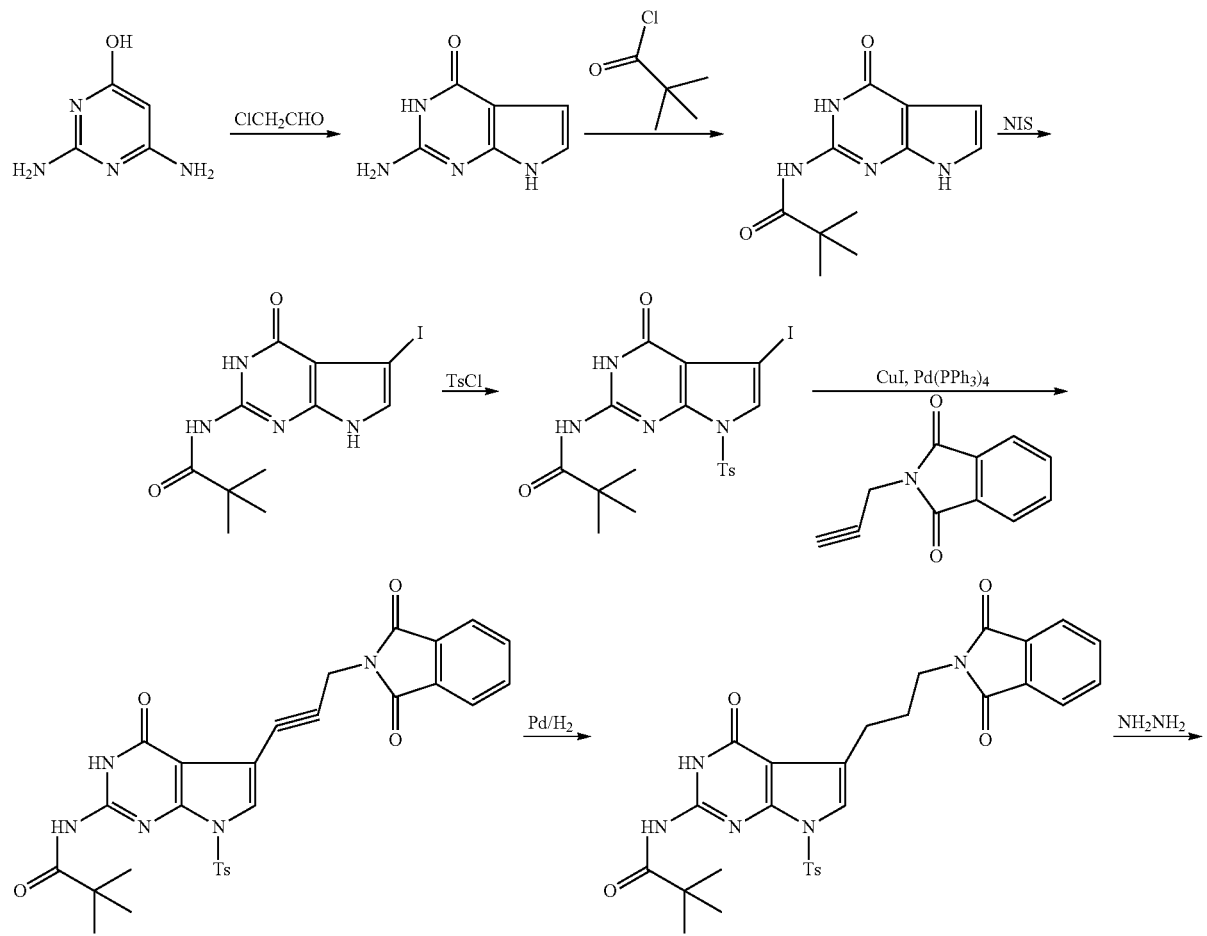

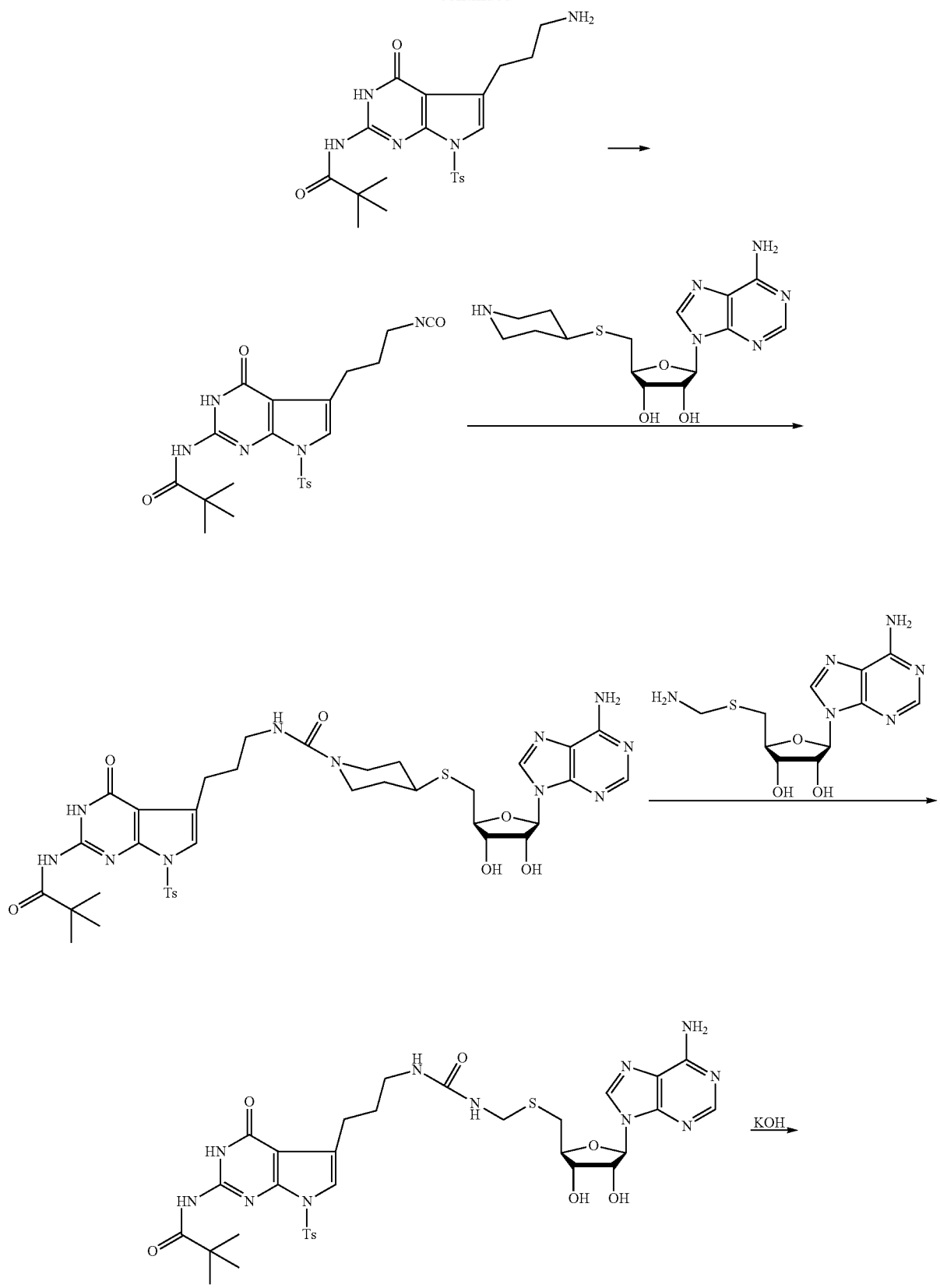

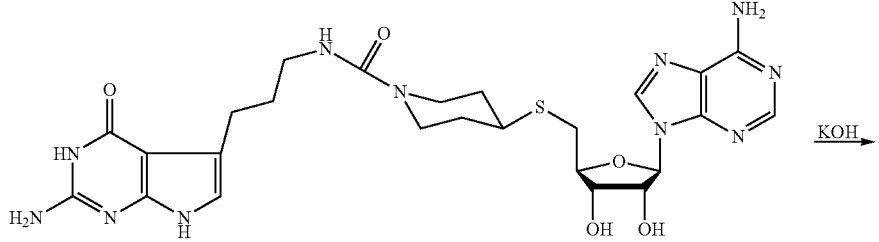

125

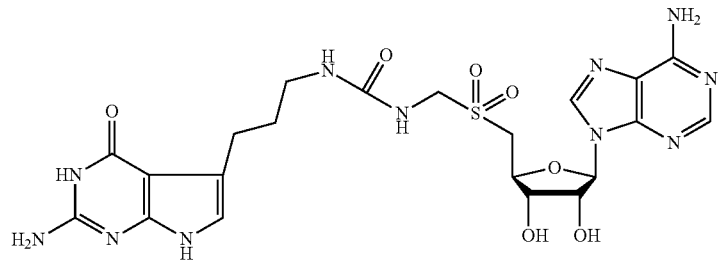

126

Example 8

Biochemical Studies

Binding studies were carried out at room temperature. Protein (HPPK) and ligand stock solutions were made in 100 mM Tris-HCl, pH 8.3, and their concentrations were determined spectrophotometrically using the following extinction coefficients: 21600 $M^{-1}$ $cm^{-1}$ at 280 nm for HPPK and 7124 $M^{-1}$ $cm^{-1}$ at 380 nm for the tetrahydropteridine bisubstrate inhibitors of Formula I. A 3-mL dilute inhibitor solution in a fluorometric cuvette was titrated with the protein stock solution. Fluorescence was measured on a Horiba Jobin Yvon FluoroMax-4 fluorometer. The excitation wavelength and slit were 364-380 and 2-3 nm, respectively, and the emission wavelength and slit were 450-482 and 2-5 nm, respectively. A few HPPK preparations showed some fluorescence at the excitation and emission wavelengths. For these HPPK preparations, a control experiment, in which a 3-mL buffer solution was titrated with the protein solution, was performed. The control data was subtracted from the titration data. The corrected titration data was then analyzed by nonlinear least-squares regression using the software Origin and the equation:

$$F_{obs} = \varepsilon_f L_t + \frac{(\varepsilon_b - \varepsilon_f)\left(L_t + E_t + K_d - \sqrt{(L_t + E_t + K_d)^2 - 4E_t L_t}\right)}{2}$$

where $F_{obs}$ is the observed fluorescence, $\varepsilon_f$ and $\varepsilon_b$ are the fluorescence coefficients of the ligand in the free and protein-bound states, respectively, $L_t$ is the total concentration of the ligand, and $E_t$ is the total concentration of HPPK. $L_t$ and $E_t$ were varied during the titration process according to the following expressions:

$$L_t = \frac{L_0 V_0}{V_0 + \Delta V} \text{ and } E_t = \frac{E_0 \Delta V}{V_0 + \Delta V}$$

where $E_0$ is the concentration of the HPPK stock solution, $L_0$ is the initial concentration of the ligand, $V_0$ is the initial volume of the titration, and $\Delta V$ is the total volume of the added HPPK solution.

The $K_d$ values were obtained for certain compounds of Formula I by nonlinear least-squares analysis and are presented in the following table.

| Cpd. # | Structure | $K_d$ |
|---|---|---|
| 101 | 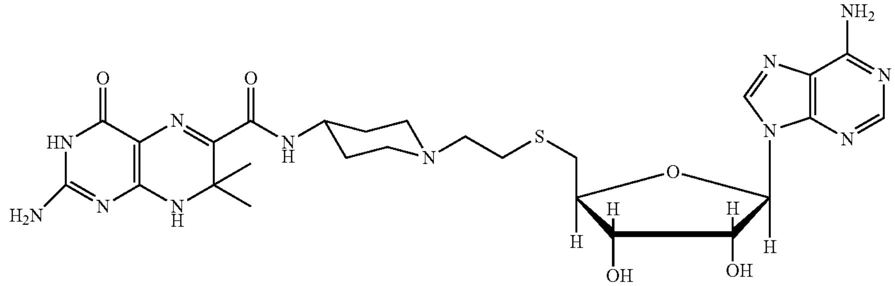 | 11.5 μM |

| Cpd. # | Structure | $K_d$ |
|---|---|---|
| 114 | 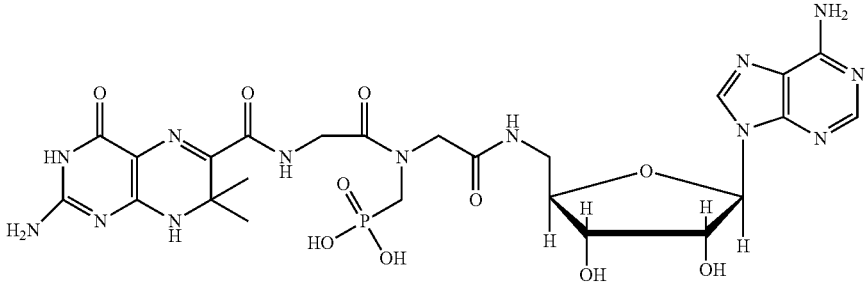 | 1.8 μM |
| 115 | 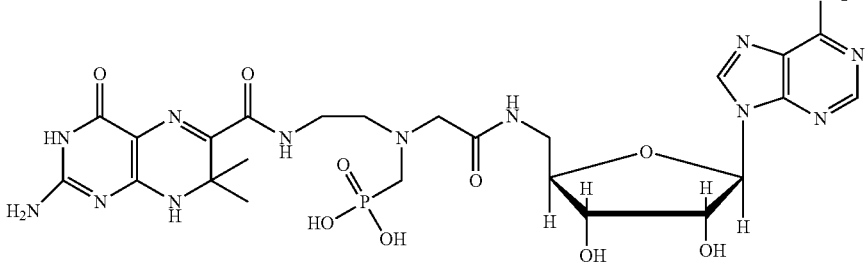 | 2.9 μM |
| 118 | 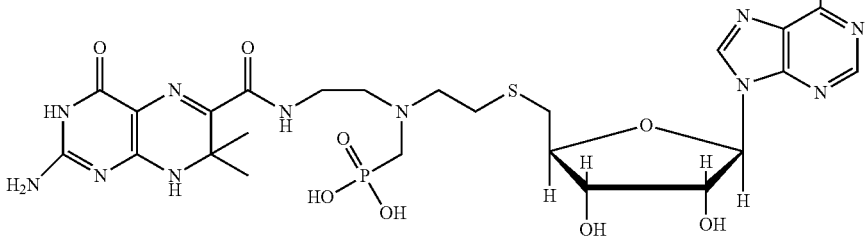 | 0.4 μM |
| 120 | 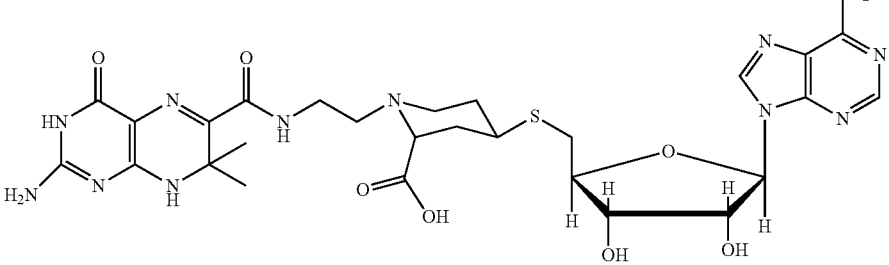 | 0.3 μM |

While specific embodiments have been shown and described, various modifications and substitutions can be made thereto without departing from the spirit and scope of the invention. Accordingly, it is to be understood that the present invention has been described by way of illustration and not limitations.

What is claimed is:

1. A compound or pharmaceutically acceptable salt thereof of the formula:

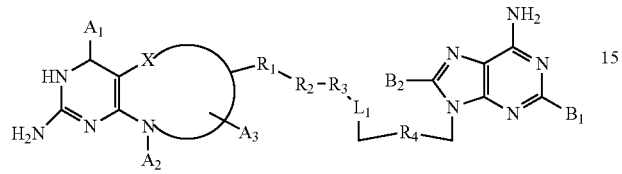

wherein:

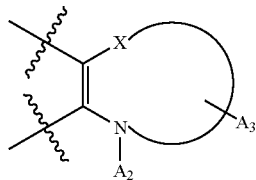

is a 5 or 6-membered heterocyclic ring;

X is nitrogen, —N(A$_5$)—, —C(A$_6$)—, or —C(A$_6$A$_7$)—;
A$_1$ is hydrogen, oxo, amino, or amino C$_1$-C$_2$alkyl;
A$_2$ is absent, hydrogen, or C$_1$-C$_2$alkyl;
A$_3$ is absent, or one or two substituents independently chosen from hydrogen, halogen, C$_1$-C$_2$alkyl, and C$_1$-C$_2$alkoxy;
A$_5$ is hydrogen or C$_1$-C$_4$alkyl;
A$_6$ and A$_7$ are independently hydrogen, C$_1$-C$_4$alkyl, or C$_1$-C$_4$alkoxy;
R$_1$ is C$_1$-C$_4$alkylene optionally substituted with hydroxyl, halogen, C$_1$-C$_2$alkyl, or oxo;
R$_2$ is chosen from —NH—, —NHC(=O)—, —SH—, —S(=O)—, —S(=O)$_2$—, —P(=O)—, and —P(=O)$_2$—;
R$_3$ is —N(R$_5$—), —(C$_1$-C$_4$alkyl)N(R$_5$)—, or —(C$_1$-C$_4$alkyl)C(O)N(R$_5$)—, where R$_5$ is alkyl substituted with —P(O)(OH)$_2$, —OP(O)(OH)$_2$, or —COOH;
R$_3$ is a 5- or 6-membered heterocycloalkyl containing 1 or 2 heteroatoms independently chosen from N, O, and S, which 5- or 6-membered heterocycloalkyl is unsubstituted or substituted with 1 or more substituents independently chosen from hydroxyl, halogen, amino, —COOH, C$_1$-C$_4$alkyl, C$_1$-C$_4$alkoxy, mono- and di-C$_1$-C$_4$alkylamino, C$_1$-C$_2$haloalkyl, and C$_1$-C$_2$haloalkoxy; or
R$_3$ is —(C$_1$-C$_4$alkyl)heterocycloalkyl; which heterocycloalkyl is a 5- or 6-membered heterocycloalkyl containing 1 or 2 heteroatoms independently chosen from N, O, and S, and is substituted with at least one —(C$_0$-C$_4$alkyl)P(O)(OH)$_2$, —(C$_0$-C$_4$alkyl)OP(O)(OH)$_2$, —(C$_0$-C$_4$alkyl)COOH, or —(C$_0$-C$_4$alkyl)C(=O)O(C$_1$-C$_4$alkyl) and optionally substituted with 1 or more substituents independently chosen from hydroxyl, halogen, amino, —COOH, C$_1$-C$_4$alkyl, C$_1$-C$_4$alkoxy, mono- and di-C$_1$-C$_4$alkylamino, C$_1$-C$_2$haloalkyl, and C$_1$-C$_2$haloalkoxy;

L$_1$ is an alkylene linker having from 1 to 4 carbon atoms and containing 1 group selected from —O—, —NH—, —S—, —S(=O)—, —S(=O)$_2$—, —S(=O)$_2$NH—, —C(=O)NH—, —P(=O)—, and —P(=O)$_2$—; and optionally containing 1 to 2 carbon-carbon double bonds, wherein L$_1$ is unsubstituted or substituted with 1 or more substituents independently chosen from hydroxyl, halogen, amino, C$_1$-C$_4$alkyl, C$_1$-C$_4$alkoxy, C$_1$-C$_2$haloalkyl, and C$_1$-C$_2$haloalkoxy;

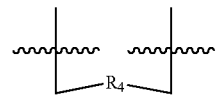

is a 5- or 6-membered monosaccharide ring;

B$_1$ and B$_2$ are independently chosen from hydrogen, halogen, hydroxyl, amino, C$_1$-C$_2$alkyl, C$_1$-C$_2$alkoxy, mono- or di-C$_1$-C$_2$alkylamino, amino C$_1$-C$_2$alkyl, C$_1$-C$_2$haloalkyl, and C$_1$-C$_2$haloalkoxy; and when

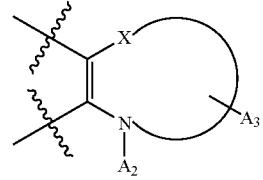

is a 6-membered heterocyclic ring, and R$_3$ is a 6-membered heterocycloalkyl containing 1 heteroatom chosen from N, O, and S and is connected to R$_2$ by a C$_1$-C$_4$alkyl group, then the 6-membered heterocycloalkyl is substituted with 1 or more substituents independently chosen from hydroxyl, halogen, amino, —COOH, —COOMe, C$_1$-C$_4$alkyl, C$_1$-C$_4$alkoxy, mono- and di-C$_1$-C$_4$alkylamino, C$_1$-C$_2$haloalkyl, and C$_1$-C$_2$haloalkoxy.

2. A compound or salt of claim 1 of the formula

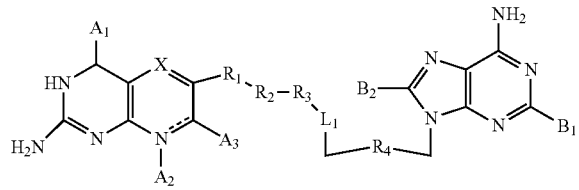

wherein

A$_2$ is absent or hydrogen;
A$_3$ is one or two substituents independently chosen from hydrogen and C$_1$-C$_2$alkyl; and
X is N or —C(A$_6$)—.

3. A compound or salt of claim 1 of the formula

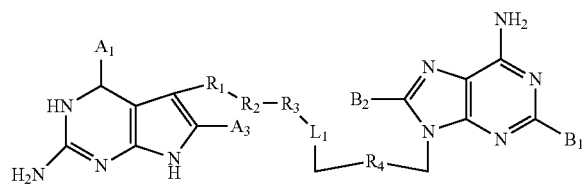

wherein
$A_3$ is one or two substituents independently chosen from hydrogen and $C_1$-$C_2$alkyl.

4. A compound or salt of claim 1 of the formula

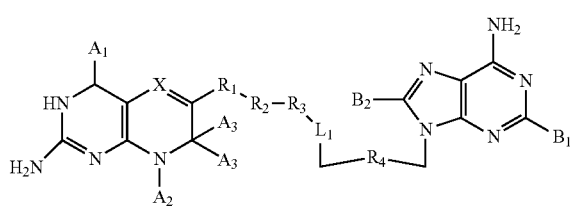

wherein:
$A_3$ are each independently hydrogen, halogen, methyl, or methoxy.

5. A compound or salt of claim 1 of the formula

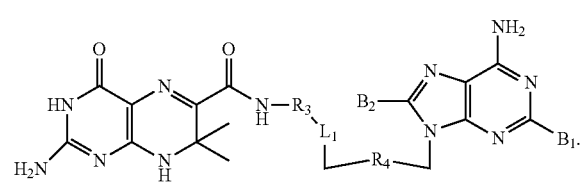

6. A compound or salt of claim 1 of the formula

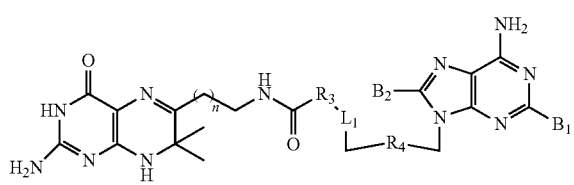

where n is 0, 1, 2, or 3.

7. A compound or salt of claim 1 of the formula

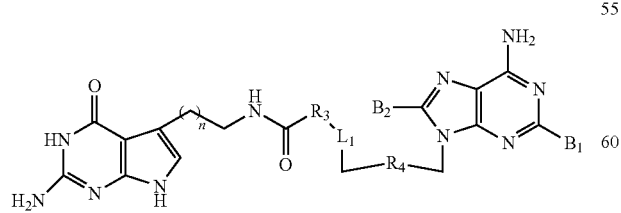

where n is 0, 1, 2, or 3.

8. A compound or salt of claim 1, wherein $B_1$ and $B_2$ are both hydrogen, and

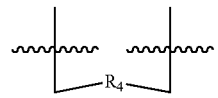

is a 5-membered monosaccharide ring.

9. A compound or salt of claim 1 of the formula:

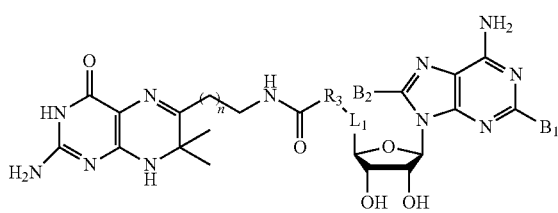

where n is 0, 1, 2, or 3.

10. A compound of salt of claim 1 of the formula

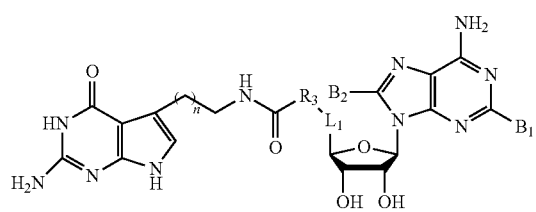

where n is 0, 1, 2, or 3.

11. A compound or salt of claim 1, wherein
$R_3$ is a 5- or 6-membered heterocycloalkyl containing 1 or 2 heteroatoms independently chosen from N, O, and S, which — or 6-membered heterocycloalkyl is unsubstituted or substituted with 1 or more substituents independently chosen from hydroxyl, halogen, amino, —COOH, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy; or
$R_3$ is —N($R_5$)—, —($C_1$-$C_4$alkyl)N($R_5$)—, or —($C_1$-$C_4$alkyl)C(O)N($R_5$)—, wherein $R_5$ is $C_1$-$C_4$alkyl substituted with —P(O)(OH)$_2$, —OP(O)(OH)$_2$, or —COOH; and
when

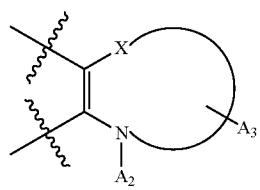

is a 6-membered heterocyclic ring, and $R_3$ is a 6-membered heterocycloalkyl containing 1 heteroatom chosen from N, O, and S and is connected to $R_2$ by a $C_1$-$C_4$alkyl group, then the 6 membered heterocycloalkyl is substituted with 1 or more substituents independently chosen from hydroxyl, halogen, amino, —COOH, —COOMe, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

12. A compound or salt of claim 11, wherein
R$_3$ is piperazine, which R$_3$ is unsubstituted or substituted with one —COOH group; or
R$_3$ is
—CH$_2$CH$_2$C(O)N(CH$_2$P(O)(OH)$_2$)—;
—CH$_2$C(O)N(CH$_2$P(O)(OH)$_2$)—;
—CH$_2$CH$_2$N(CH$_2$P(O)(OH)$_2$)—; or
—N(CH$_2$)P(O)(OH)$_2$)—.

13. A compound or salt of claim 1, wherein
L$_1$ is an alkylene linker having 1 to 4 carbon atoms and containing 1 group selected from —S—, —S(=O)—, —S(=O)$_2$—, —S(=O)$_2$NH—, and —C(=O)NH—.

14. A compound or salt of claim 13, wherein L$_1$ is chosen from

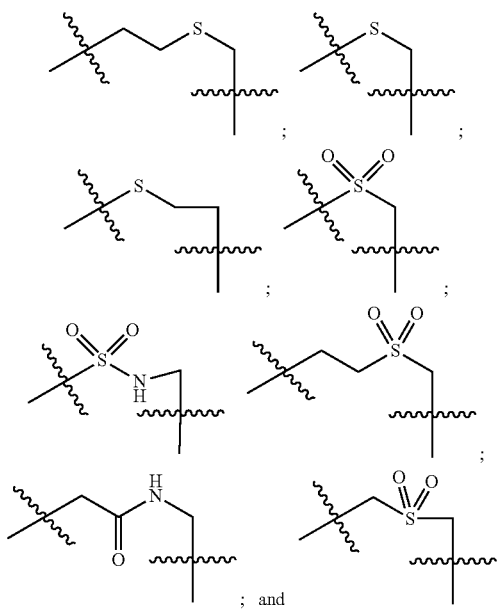

15. A compound or salt of claim 14, wherein
R$_3$ is —(C$_1$-C$_4$alkyl)piperazine, each of which piperidine or piperazine is unsubstituted or substituted with 1 or 2 —COOH groups.

16. A compound or salt of claim 1, wherein
R$_3$ is —(C$_1$-C$_4$alkyl)heterocycloalkyl; which heterocycloalkyl is a 5- or 6-membered heterocycloalkyl containing 1 or 2 heteroatoms independently chosen from N, O, and S, and is substituted with at least one —(C$_0$-C$_4$alkyl)P(O)(OH)$_2$, —(C$_0$-C$_4$alkyl)OP(O)(OH)$_2$, —(C$_0$-C$_4$alkyl)COOH, or —(C$_0$-C$_4$alkyl)C(=O)O(C$_1$-C$_4$alkyl), and optionally substituted with 1 or more substituents independently chosen from hydroxyl, halogen, amino, —COOH, C$_1$-C$_4$alkyl, C$_1$-C$_4$alkoxy, mono- and di-C$_1$-C$_4$alkylamino, C$_1$-C$_2$haloalkyl, C$_1$-C$_2$haloalkoxy; and
when

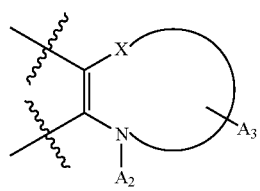

is a 6-membered heterocyclic ring, and R$_3$ is a 6-membered heterocycloalkyl containing 1 heteroatom chosen from N, O, and S and is connected to R$_2$ by a C$_1$-C$_4$alkyl group, then the 6-membered heterocycloalkyl is substituted with 1 or more substituents independently chosen from hydroxyl, halogen, amino, —COOH, —COOMe, C$_1$-C$_4$alkyl, C$_1$-C$_4$alkoxy, mono- and di-C$_1$-C$_4$alkylamino, C$_1$-C$_2$haloalkyl, and C$_1$-C$_2$haloalkoxy.

17. A compound or salt thereof of claim 1, wherein the compound is chosen from

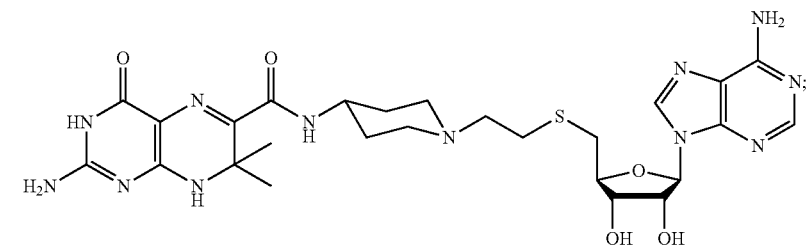

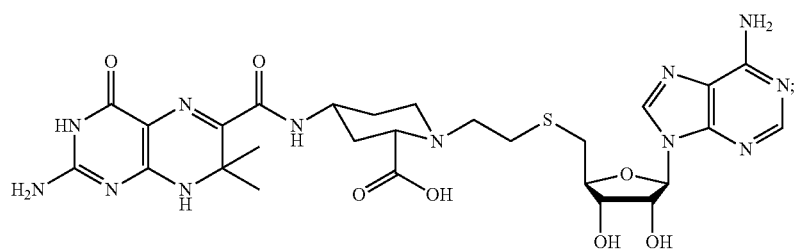

-continued
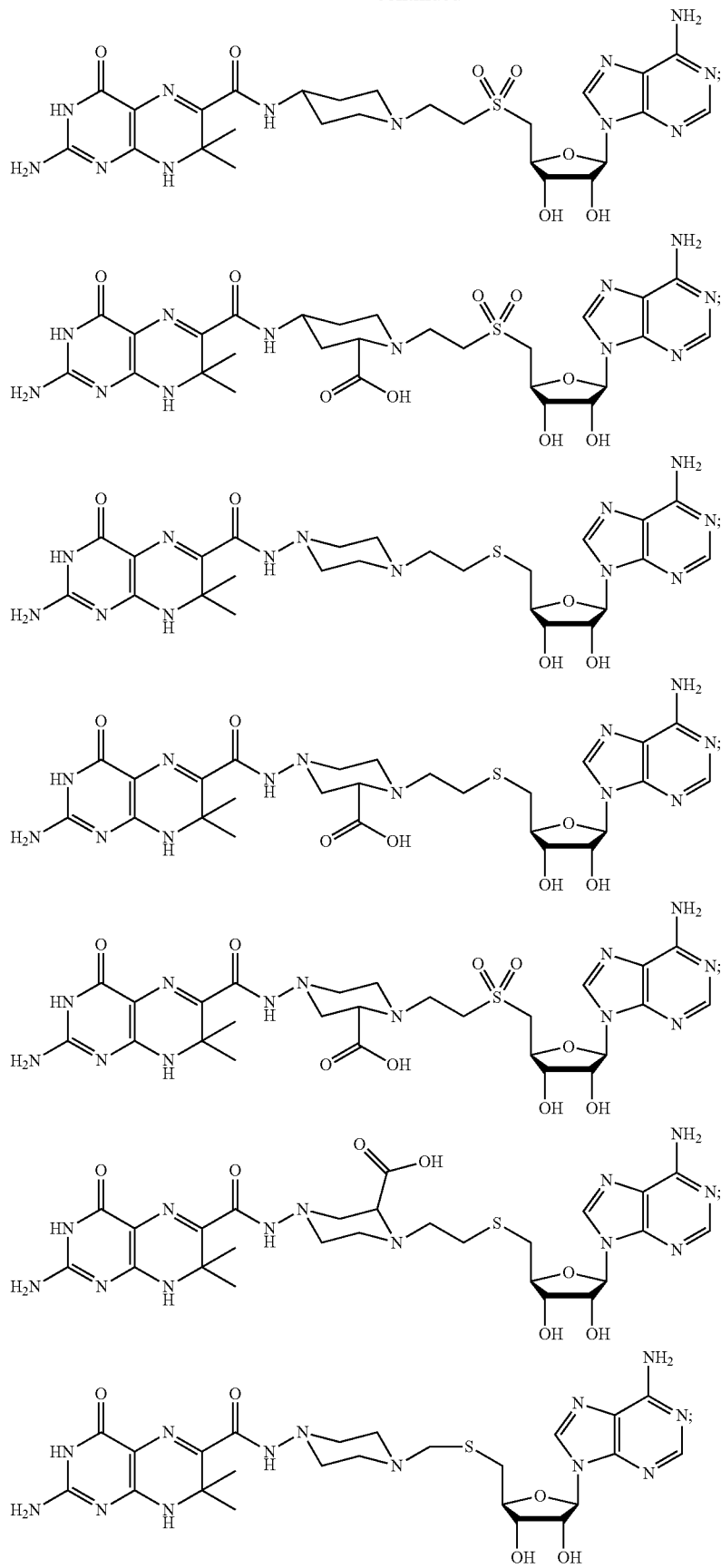

-continued
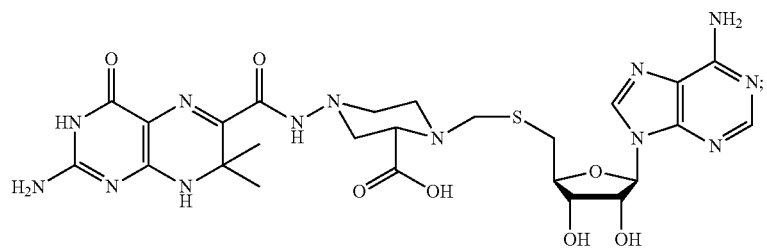
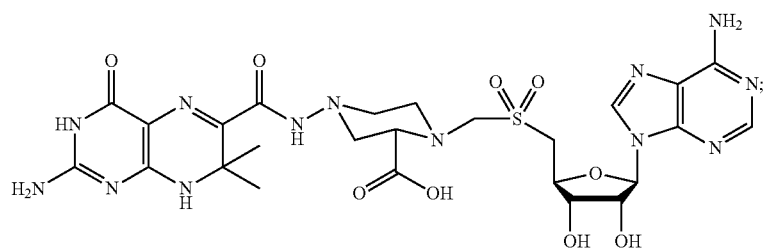
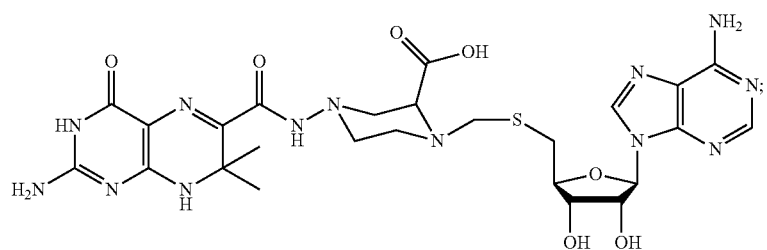
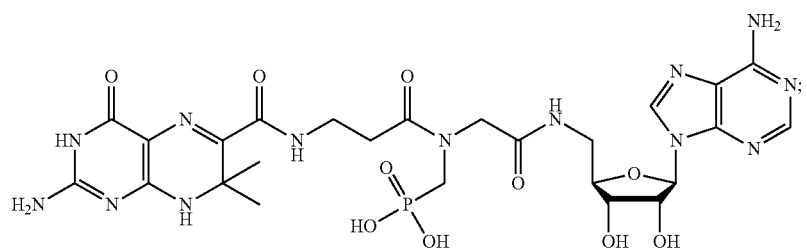
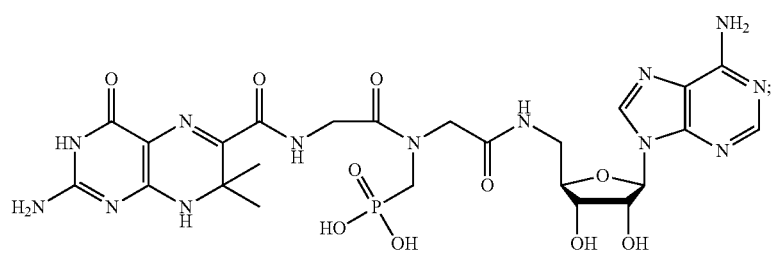
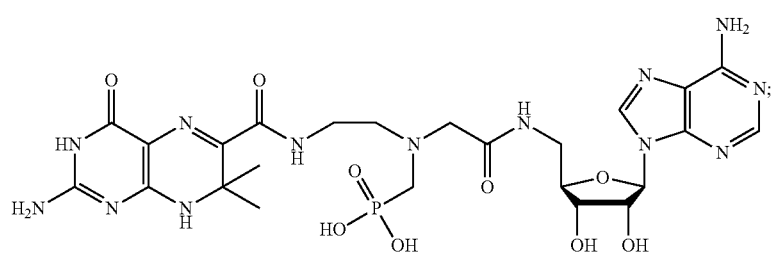

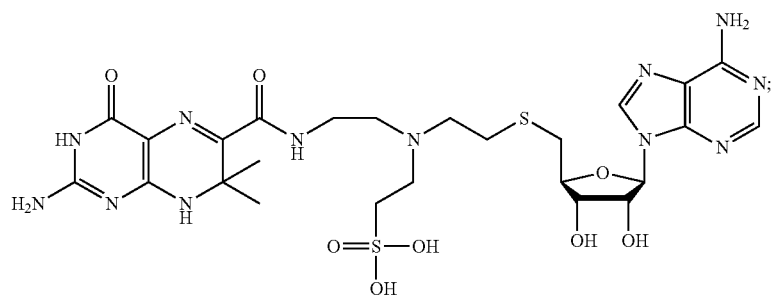
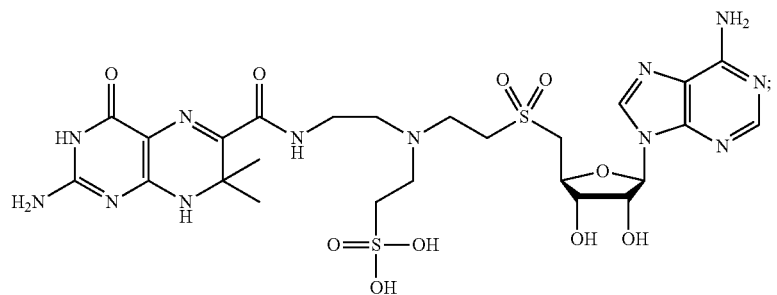
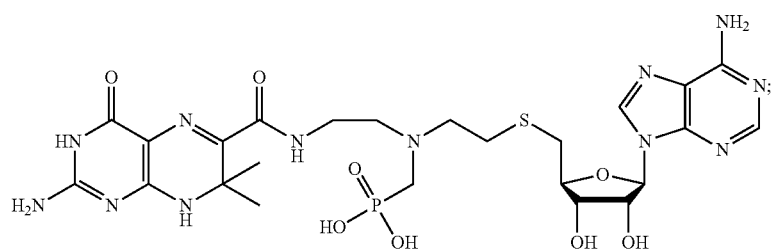
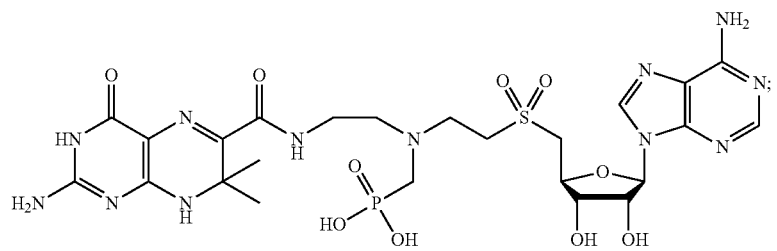
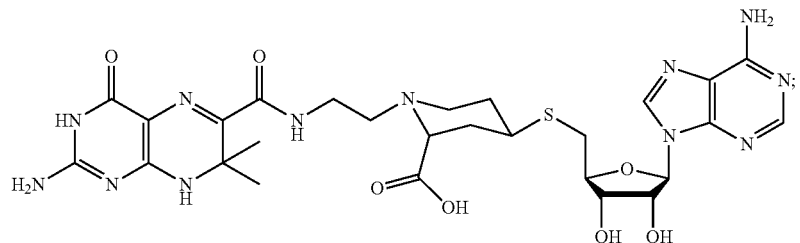
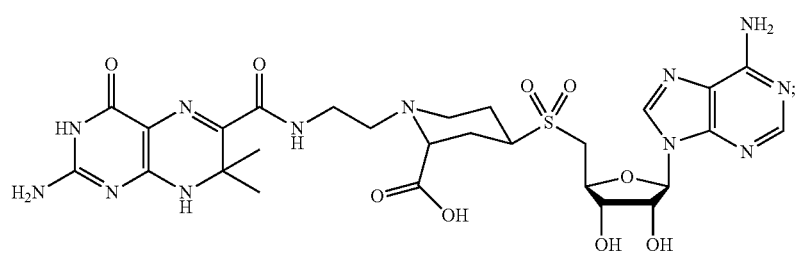

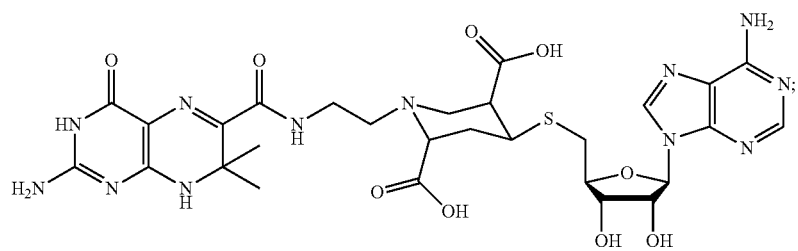
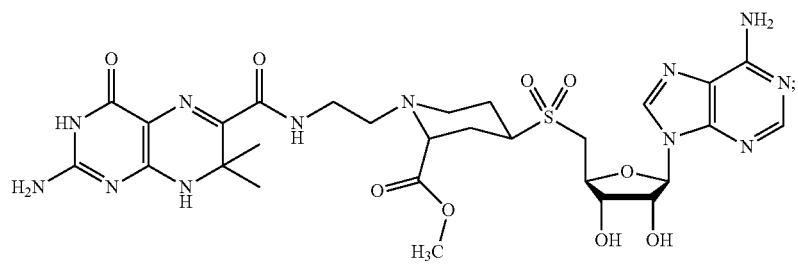
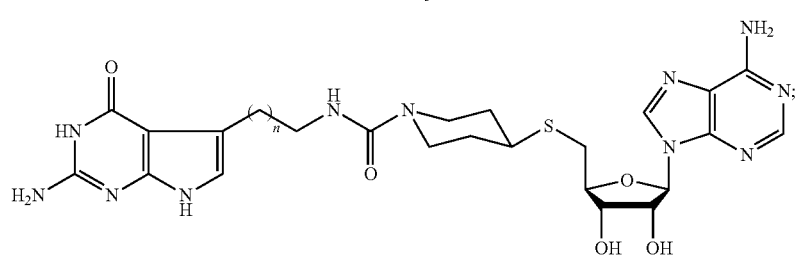
(*n* = 1 or 2)
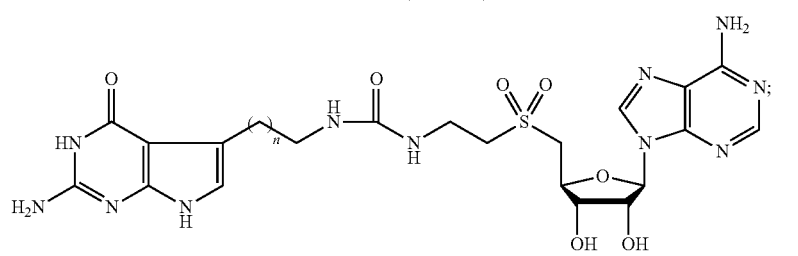
(*n* = 1 or 2)
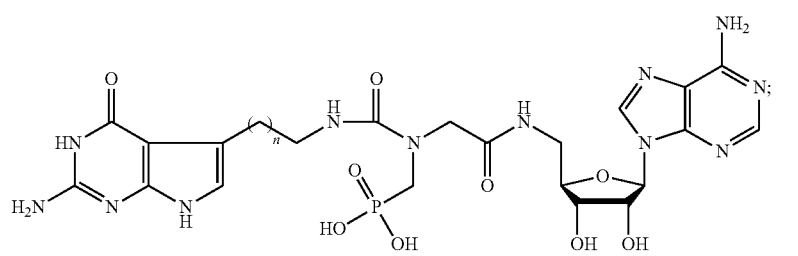
(*n* = 1 or 2)
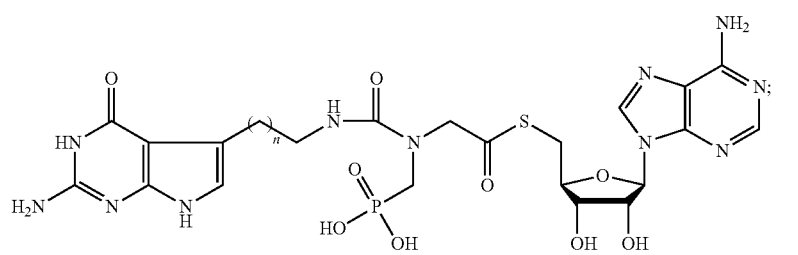
(*n* = 1 or 2)

-continued
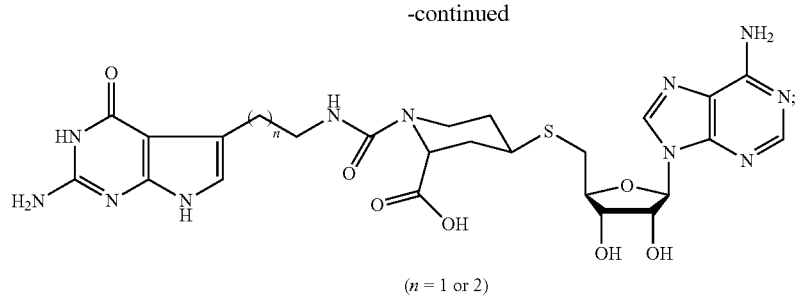
(n = 1 or 2)
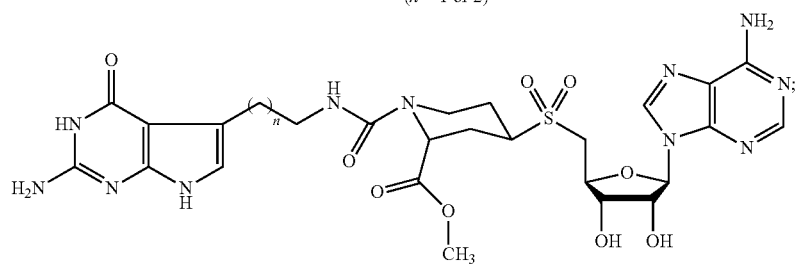
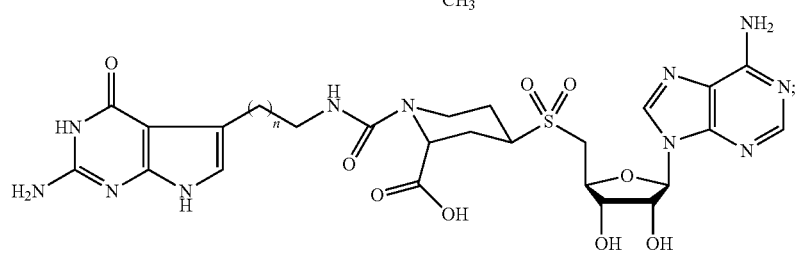
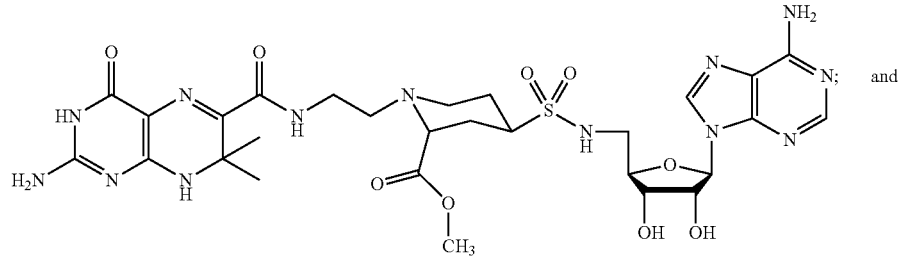 and
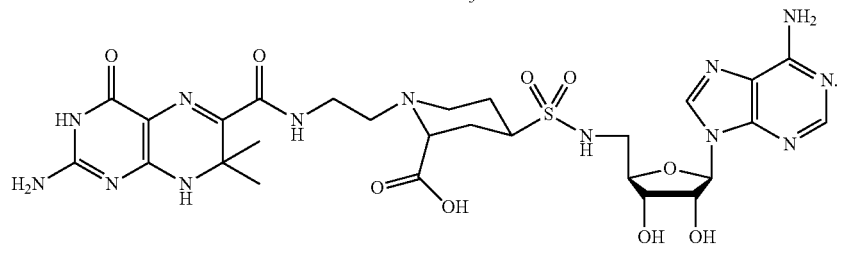
18. A pharmaceutical composition comprising a compound or salt of claim 1 and a pharmaceutically acceptable carrier.
19. A method of treating a bacterial infection, the method comprising providing a therapeutically effective amount of compound of claim 1 to a patient having a bacterial infection.
* * * * *